United States Patent
Lee et al.

(10) Patent No.: US 8,440,914 B2
(45) Date of Patent: May 14, 2013

(54) LIQUID CRYSTALLINE THERMOSET OLIGOMER OR POLYMER AND THERMOSETTING COMPOSITION AND SUBSTRATE INCLUDING THE SAME

(75) Inventors: Jae-Jun Lee, Suwon-si (KR); Kalinina Fedosya, Ulan-Ude (KR); Myung-Sup Jung, Seongnam-si (KR)

(73) Assignees: Samsung Electronics Co., Ltd. (KR); Samsung Electro-Mechanics Co., Ltd. (KR); Samsung Fine Chemicals Co., Ltd. (KR)

( * ) Notice: Subject to any disclaimer, the term of this patent is extended or adjusted under 35 U.S.C. 154(b) by 340 days.

(21) Appl. No.: 12/966,386

(22) Filed: Dec. 13, 2010

(65) Prior Publication Data

US 2011/0232944 A1   Sep. 29, 2011

(30) Foreign Application Priority Data

Mar. 26, 2010   (KR) .................. 10-2010-0027565

(51) Int. Cl.
*H05K 1/00*   (2006.01)

(52) U.S. Cl.
USPC ............ 174/254; 174/255; 428/1.6; 428/396; 428/417; 528/59; 528/170; 252/299.01; 252/299.6; 252/299.61; 252/299.62; 252/299.64

(58) Field of Classification Search .................. 174/254, 174/255; 428/1.6, 396, 417; 252/299.01, 252/299.6, 299.61, 299.62, 299.64; 528/59, 528/170
See application file for complete search history.

(56) References Cited

U.S. PATENT DOCUMENTS

| 5,085,807 A | 2/1992 | Okamoto et al. |
| 5,114,612 A * | 5/1992 | Benicewicz et al. ..... 252/299.01 |

(Continued)

FOREIGN PATENT DOCUMENTS

| JP | 63-264628 A | 11/1988 |
| JP | 2003-128928 A | 5/2003 |

(Continued)

OTHER PUBLICATIONS

Darshan et al., Synthesis, Characterization, and Thermal Properties of Tris (3-Aminophenyl) Phosphine Oxide-Based Nadimide Resins, J. Applied Polymer Science, 2008, vol. 107; Issue 3; 1628-1634.

Wang, C. et al., Synthesis and Properties of Phosphorus Containing Polyester-Amides Derived from 1,4-Bis(3- aminobenzoyloxy)-2-(6-oxido-6H-dibenz<1,2>oxaphosphorin-6-yl) Phenylene, J. of Polymer Science: Part A: Polymer Chemistry, 1999, vol. 37; pp. 891-899.

(Continued)

*Primary Examiner* — Xiaoliang Chen
(74) *Attorney, Agent, or Firm* — Cantor Colburn LLP

(57) ABSTRACT

A liquid crystalline thermoset oligomer or polymer including a structural unit of Chemical Formulae 1 and 2; and a functional group of Chemical Formula A,

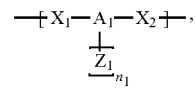

[Chemical Formula 1]

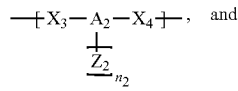

[Chemical Formula 2]

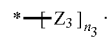

[Chemical Formula A]

20 Claims, 1 Drawing Sheet

U.S. PATENT DOCUMENTS

| | | | |
|---|---|---|---|
| 5,904,984 A * | 5/1999 | Smith et al. | 428/396 |
| 6,939,940 B2 | 9/2005 | Dingemans et al. | |
| 8,101,248 B2 * | 1/2012 | Yun et al. | 428/1.6 |
| 2005/0209429 A1 | 9/2005 | Dingemans et al. | |
| 2010/0292232 A1 * | 11/2010 | Elleder et al. | 514/233.2 |

FOREIGN PATENT DOCUMENTS

| | | |
|---|---|---|
| JP | 2006-063258 A | 3/2006 |
| KR | 1020030045804 A | 6/2003 |

OTHER PUBLICATIONS

Yang, M. et al., A novel phosphorus-containing thermotropic liquid crystalline poly(ester-imide) with high flame retardancy, Polymers for Advanced Technologies, 2009, vol. 20, Issue 4; 378-383.

Zhao, C.-S. et al., A Phosphorus-Containing Thermotropic Liquid Crystalline Copolyester with Low Mesophase Temperature and High Flame Retardance, J. of Polymer Science Part A: Polymer Chemistry, 2008, vol. 46, Issue 17; 5752-5759.

* cited by examiner

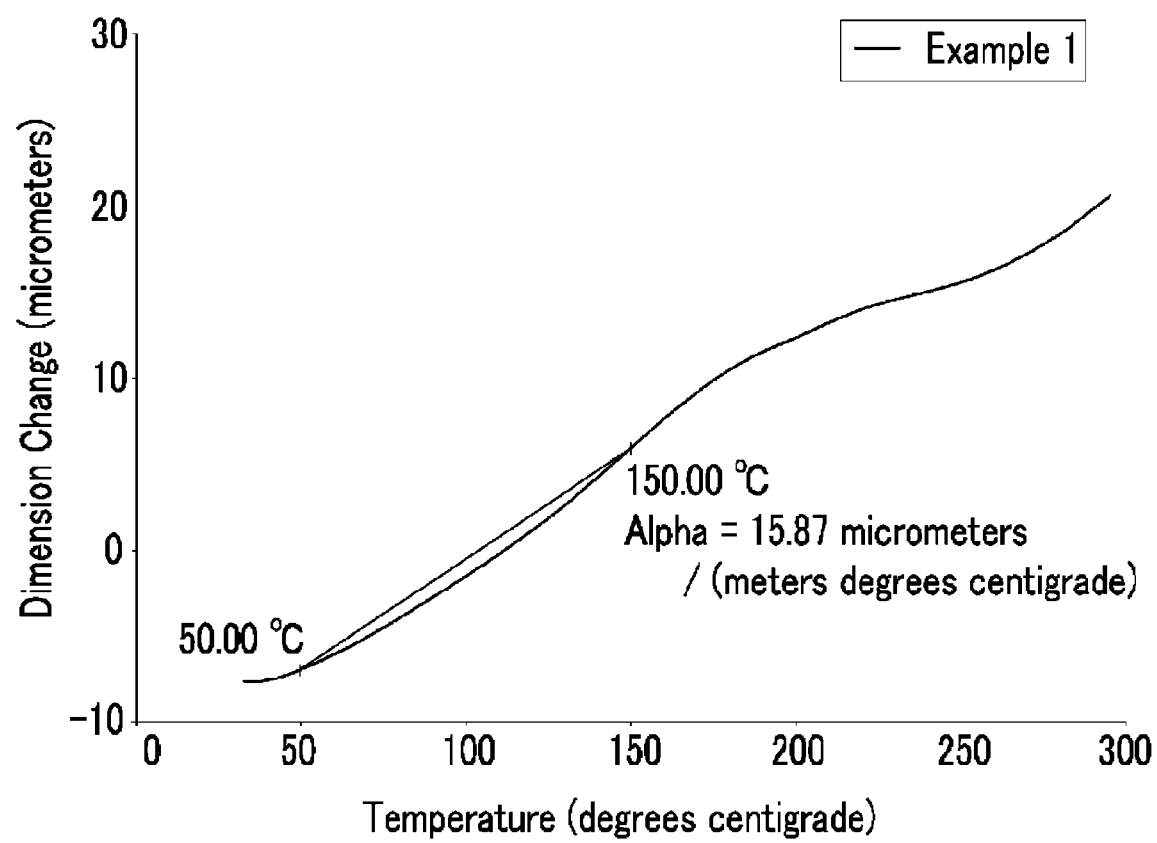

LIQUID CRYSTALLINE THERMOSET OLIGOMER OR POLYMER AND THERMOSETTING COMPOSITION AND SUBSTRATE INCLUDING THE SAME

BACKGROUND

1. Field

This disclosure relates to a liquid crystalline thermoset oligomer or polymer, a thermosetting composition, and a board including the same.

2. Description of the Related Art

Electronic devices such as computers, semiconductor devices, displays, and communication devices include printed electronic circuit boards. A printed electronic circuit board may include signal lines for transferring signals, an insulation layer for preventing a short circuit between the signal lines, a switching element, and the like. It may be desirable for a printed electronic circuit board to be a thin film to improve the performance of the electronic devices, and the printed electronic circuit board may have a very small size. The printed electronic circuit board may have other performance specifications. Thus there remains a need for an improved thermoset oligomer or polymer.

SUMMARY

An aspect of this disclosure provides a liquid crystalline thermoset ("LCT") oligomer or polymer having improved heat resistance and mechanical strength, a low dielectric constant, and low hygroscopicity, as well as excellent flame retardance and adherence.

Another aspect of this disclosure provides a board-forming composition including the liquid crystalline thermoset oligomer or polymer.

Yet another aspect of this disclosure provides a prepreg, a film, and a flexible printed circuit ("FPC") having improved heat resistance and mechanical strength, a low dielectric constant, and low hygroscopicity, as well as excellent flame retardance and adherence.

According to an aspect of this disclosure, a liquid crystalline thermoset oligomer or polymer is provided that includes structural units represented by the following Chemical Formulae 1 and 2; and a functional group of Chemical Formula A at at least one terminal end,

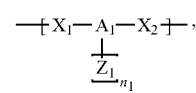

[Chemical Formula 1]

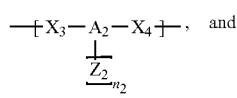

and [Chemical Formula 2]

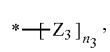

[Chemical Formula A]

wherein, in Chemical Formulae 1, 2, and A, $X_1$ to $X_4$ are the same or different, and are C(=O)O, O, C(=O)NR', NR', or CO, wherein R and R' are the same or different, and are hydrogen, a substituted or unsubstituted C1 to C20 alkyl group, or a substituted or unsubstituted C6 to C30 aryl group, $Z_1$ to $Z_3$ are the same or different, and are a hydroxyl group, a thiol group, a substituted or unsubstituted maleimide group, a substituted or unsubstituted nadimide group, a substituted or unsubstituted tetrahydrophthalimide group, a substituted or unsubstituted C2 to C30 alkenyl group, a substituted or unsubstituted C2 to C30 alkynyl group, a substituted or unsubstituted propargyl ether group, a substituted or unsubstituted benzocyclobutene group, an (iso)cyanate group, a cyanide group, a substituted or unsubstituted C3 to C30 alicyclic group including a double bond or a triple bond, a substituted or unsubstituted heteroatom-containing C3 to C30 alicyclic group including a double bond or a triple bond, a C3 to C30 alicyclic group including a C2 to C30 alkenyl group or a C2 to C30 alkynyl group, a heteroatom-containing C3 to C30 alicyclic group including a C2 to C30 alkenyl group or a C2 to C30 alkynyl group, a C6 to C30 aryl group including a C2 to C30 alkenyl group or a C2 to C30 alkynyl group, a C6 to C30 aryl group including an (iso)cyanate group or a cyanide group, or a combination thereof, $n_1$ to $n_3$ are the same or different, and are integers ranging from 0 to about 3, and the sum $n_1+n_2+n_3$ is 1 or more, $A_1$ is a functional group represented by the following Chemical Formulae 4-1 to 4-7, and $A_2$ is a functional group represented by the following Chemical Formulae 5-1 to 5-6 or is a C2 to C20 alkylene group including a functional group represented by the following Chemical Formula 6,

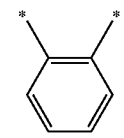

[Chemical Formula 4-1]

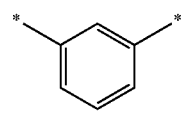

[Chemical Formula 4-2]

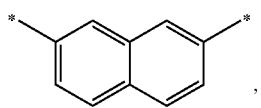

[Chemical Formula 4-3]

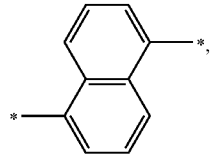

[Chemical Formula 4-4]

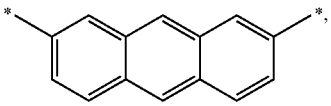

[Chemical Formula 4-5]

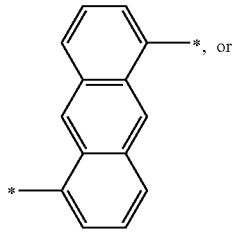

[Chemical Formula 4-6]

[Chemical Formula 4-7]

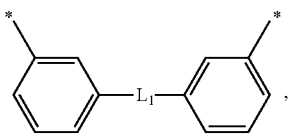

wherein, in Chemical Formula 4-7, $L_1$ is a divalent substituted or unsubstituted hydrocarbon group, and wherein in Chemical Formulae 4-1 to 4-7, at least one hydrogen of each aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$ (wherein $Z_1$ is the same as defined in Chemical Formula 1),

[Chemical Formula 5-1]

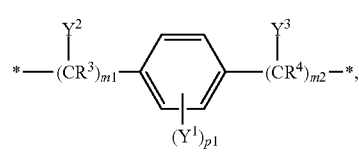

wherein, in Chemical Formula 5-1, $Y^1$ to $Y^3$ are the same or different, and are hydrogen, a C1 to C10 alkyl group, or a functional group represented by the following Chemical Formula 6, provided that at least one of $Y^1$ to $Y^3$ is the functional group represented by the following Chemical Formula 6, p1 is an integer ranging from 0 to 4, m1 and m2 are the same or different, and are integers ranging from 0 to 3, provided that p1, m1, and m2 are not simultaneously zero (0), and $R^3$ and $R^4$ are the same or different, and are hydrogen or a C1 to C10 alkyl group,

[Chemical Formula 5-2]

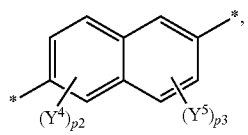

wherein, in Chemical Formula 5-2, $Y^4$ and $Y^5$ are the same or different, and are hydrogen, a C1 to C10 alkyl group, or a functional group represented by the following Chemical Formula 6, provided that at least one of $Y^4$ and $Y^5$ is the functional group represented by the following Chemical Formula 6, and p2 and p3 are the same or different, and are integers ranging from 0 to 3, provided that p2 and p3 are not simultaneously zero (0).

[Chemical Formula 5-3]

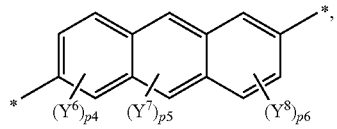

wherein in Chemical Formula 5-3, $Y^6$ to $Y^8$ are the same or different, and are hydrogen, a C1 to C10 alkyl group, or a functional group represented by the following Chemical Formula 6, provided that at least one of $Y^8$ to $Y^8$ is the functional, group represented by the following Chemical Formula 6, and p4 and p6 are the same or different, and are integers ranging from 0 to 3, p5 is an integer ranging from 0 to 2, provided that p4, p5, and p6 are not simultaneously zero (0),

[Chemical Formula 5-4]

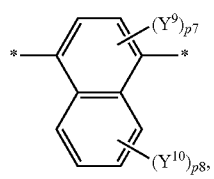

wherein in Chemical Formula 5-4, $Y^9$ and $Y^{10}$ are the same or different, and are hydrogen, a C1 to C10 alkyl group, or a functional group represented by the following Chemical Formula 6, provided that at least one of $Y^9$ and $Y^{10}$ is the functional group represented by the following Chemical Formula 6, and p7 and p8 are the same or different, and are integers ranging from 0 to 2, provided that p7 and p8 are not simultaneously zero (0),

[Chemical Formula 5-5]

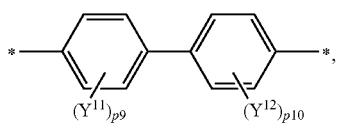

wherein in Chemical Formula 5-5, $Y^{11}$ and $Y^{12}$ are the same or different, and are hydrogen, a C1 to C10 alkyl group, or a functional group represented by the following Chemical Formula 6, provided that at least one of $Y^{11}$ and $Y^{12}$ is the functional group represented by the following. Chemical Formula 6, and p9 and p10 are the same or different, and are integers ranging from 0 to 4, provided that p9 and p10 are not simultaneously zero (0),

[Chemical Formula 5-6]

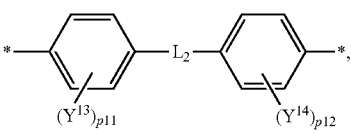

wherein, in Chemical Formula 5-6, $Y^{13}$ and $Y^{14}$ are the same or different, and are hydrogen, a C1 to C10 alkyl group, or a functional group represented by the following Chemical Formula 6, provided that at least one of $Y^{13}$ and $Y^{14}$ is the functional group represented by the following Chemical Formula 6, p11 and p12 are integers ranging from 0 to 4, and $L_2$ is an ether group, a sulfide group, a ketone group, an amide group, a sulfoxide group, a sulfone group, an azo group, an imine group, a substituted or unsubstituted C1 to C20 alkylene group, a substituted or unsubstituted C2 to C20 alkenylene group, a substituted or unsubstituted C6 to C30 arylene group, a divalent hydrocarbon group which is unsubstituted or substituted with at least one functional group represented by Chemical Formula 6, or a divalent hydrocarbon group of Chemical Formulae 7-1 to 7-3, provided that both p11 and p12 are not zero (0) when $L_2$ is unsubstituted with a functional group of the following Chemical Formula 6, and in Chemical Formulae 5-1 to 5-6, at least one hydrogen of each aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$ (wherein $Z_1$ is the same as defined in Chemical Formula 1),

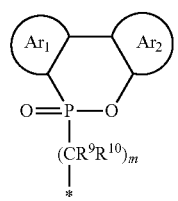
[Chemical Formula 6]

wherein, in Chemical Formula 6, $Ar_1$ and $Ar_2$ are the same or different, and are a C4 to C30 substituted or unsubstituted aromatic cyclic group, $R^9$ and $R^{10}$ are the same or different, and are hydrogen, a C1 to C20 alkyl group, or a C6 to C30 aryl group, and m is an integer ranging from 0 to about 3,

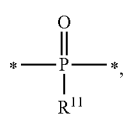
[Chemical Formula 7-1]

wherein, in Chemical Formula 7-1, $R^{11}$ is hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group,

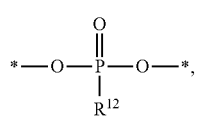
[Chemical Formula 7-2]

wherein, in Chemical Formula 7-2, $R^{12}$ is hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group

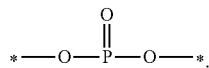
[Chemical Formula 7-3]

The liquid crystalline thermoset oligomer may have a number average molecular weight of about 500 to about 10,000 grams per mole ("g/mol"), or the liquid crystalline thermoset polymer may have a number average molecular weight of about 10,000 to about 1,000,000 g/mol.

The structural unit of Chemical Formula 1 may be included in an amount of about 5 mole percent ("mol %") to about 60 mol % based on the total amount of the liquid crystalline thermoset oligomer or polymer, and the structural unit of Chemical Formula 2 may be included in an amount of about 40 mol % to about 95 mol % based on the total amount of the liquid crystalline thermoset oligomer or polymer.

The liquid crystalline thermoset oligomer or polymer may further include the structural unit of the following Chemical Formula 3:

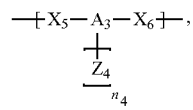
[Chemical Formula 3]

wherein, in Chemical Formula 3, $X_5$ to $X_6$ are the same or different, and are C(=O)O, O, C(=O)NR, NR', or CO, wherein R and R' are the same or different, and are hydrogen, a substituted or unsubstituted C1 to C20 alkyl group or a substituted or unsubstituted C6 to C30 aryl group, $Z_4$ is a hydroxyl group, a thiol group, a substituted or unsubstituted maleimide group, a substituted or unsubstituted nadimide group, a substituted or unsubstituted tetrahydrophthalimide group, a substituted or unsubstituted C2 to C30 alkenyl group, a substituted or unsubstituted C2 to C30 alkynyl group, a substituted or unsubstituted propargyl ether group, a substituted or unsubstituted benzocyclobutene group, an (iso)cyanate group, a cyanide group, a substituted or unsubstituted C3 to C30 alicyclic group including a double bond or a triple bond, a substituted or unsubstituted heteroatom-containing C3 to C30 alicyclic group including a double bond or a triple bond, a C3 to C30 alicyclic group including a C2 to C30 alkenyl group or a C2 to C30 alkynyl group, a heteroatom-containing C3 to C30 alicyclic group including a C2 to C30 alkenyl group or a C2 to C30 alkynyl group, a C6 to C30 aryl group including a C2 to C30 alkenyl group or a C2 to C30 alkynyl group, a C6 to C30 aryl group including an (iso)cyanate group or a cyanide group, or a combination thereof, $n_4$ is an integer ranging from 0 to about 3, and $A_3$ is a functional group represented by the following Chemical Formulae 5-7 to 5-12:

[Chemical Formula 5-7]

wherein, in Chemical Formula 5-7, m1 and m2 are the same or different, and range from 0 to 3, and $R^5$ to $R^8$ are the same or different, and are hydrogen or a C1 to C10 alkyl group,

[Chemical Formula 5-8]

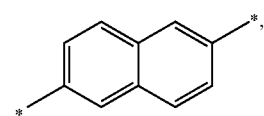

[Chemical Formula 5-9]

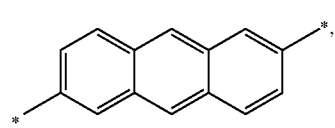

[Chemical Formula 5-10]

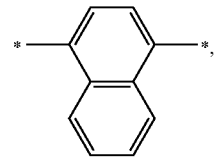

[Chemical Formula 5-11]

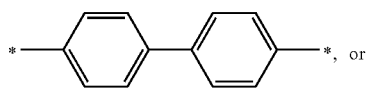, or

[Chemical Formula 5-12]

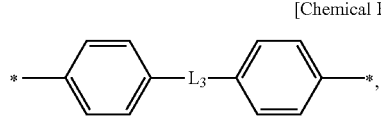, wherein, in Chemical Formula 5-12, $L_3$ is the same as $L_1$ of Chemical Formula 4-7, and in Chemical Formulae 5-7 to 5-12, at least one hydrogen of each aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$ (wherein $Z_1$ is the same as defined in Chemical Formula 1).

The structural unit of Chemical Formula 3 may be included in an amount of about 0.01 to about 20 moles, based on 1 mole of the structural unit of Chemical Formula 2.

$Z_1$ to $Z_3$ may be a thermosetting cross-linking group represented by the following Chemical Formulae 8-1 to 8-7,

[Chemical Formula 8-1]

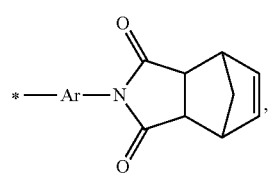

[Chemical Formula 8-2]

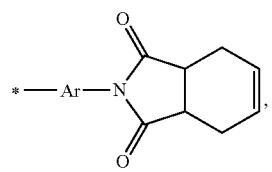

[Chemical Formula 8-3]

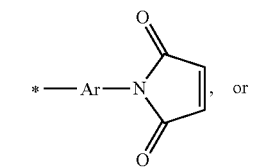, or

[Chemical Formula 8-4]

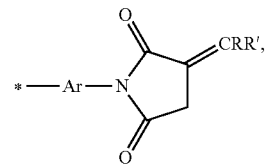

wherein, in Chemical Formula 8-4,

R and R' are the same or different, and are hydrogen, a substituted or unsubstituted C1 to C20 alkyl group, or a substituted or unsubstituted C6 to C30 aryl group,

[Chemical Formula 8-5]

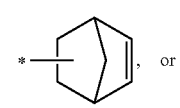, or

[Chemical Formula 8-6]

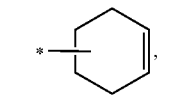, wherein, in Chemical Formulae 8-1 to 8-4,

Ar is a C6 to C30 arylene group, and in Chemical Formulae 8-1 to 8-6, at least one hydrogen of each alicyclic ring or an aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group,

[Chemical Formula 8-7]

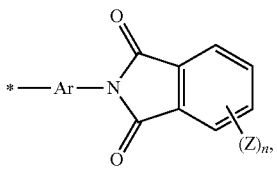

wherein, in Chemical Formula 8-7,
Ar is a C6 to C30 arylene group,
Z is a substituted or unsubstituted C2 to C20 alkenyl group, a substituted or unsubstituted C2 to C20 alkynyl group, or a substituted or unsubstituted C3 to C20 cycloalkenyl group, and
n is an integer ranging from 1 to about 4.

In an embodiment, at least one hydrogen of an aromatic ring in Chemical Formula 8-7 may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group.

$L_1$ of above Chemical Formula 4-7 may be an ether group, a sulfide group, a ketone group, an amide group, a sulfoxide group, a sulfone group, an azo group, an imine group, a substituted or unsubstituted C1 to C20 alkylene group, a substituted or unsubstituted C2 to C20 alkenylene group, a substituted or unsubstituted C6 to C30 arylene group, or a combination including at least one of the foregoing.

The functional group represented by Chemical Formula 6 may include a functional group represented by the following Chemical Formula 11:

[Chemical Formula 11]

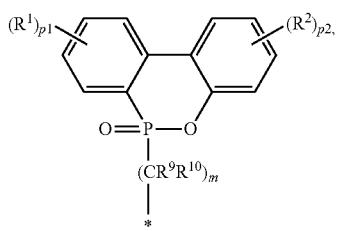

wherein, in Chemical Formula 11,
$R^1$ and $R^2$ are the same or different, and are hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$ (wherein $Z_1$ is the same as defined in Chemical Formula 1),
p1 and p2 are the same or different, and are integers ranging from 0 to 4, and
$R^9$ and $R^{10}$ are the same or different, and are hydrogen, a C1 to C20 alkyl group, or a C6 to C30 aryl group, and
m is an integer ranging from 0 to about 3.

Another aspect of this disclosure provides a thermosetting composition including the liquid crystalline thermoset oligomer or polymer, and a solvent.

Another aspect of this disclosure provides a prepreg including a polymerization product of the thermosetting composition.

Another aspect of this disclosure provides a film including a polymerization product of the thermosetting composition.

Yet another aspect of this disclosure provides a flexible printed circuit ("FPC") including a polymerization product of the thermosetting composition.

The flexible printed circuit ("FPC") may include a film, a printed board, a copper foil, a copper foil coated laminate, a prepreg, or a combination thereof. It may further include a metal layer disposed (e.g., deposited) on a surface of the prepreg, and the metal layer may include a pattern on a surface thereof.

BRIEF DESCRIPTION OF THE DRAWING

FIG. 1 is a graph of dimension change (micrometers, μm) versus temperature (degrees centigrade, ° C.) which shows the results of a coefficient of thermal expansion measurement of a prepreg specimen according to Example 1.

DETAILED DESCRIPTION

This disclosure will be described more fully hereinafter with reference to the accompanying drawings, in which embodiments are shown. This disclosure may, however, be embodied in many different forms and is not to be construed as limited to the exemplary embodiments set forth herein.

It will be understood that when an element is referred to as being "on" another element, it can be directly on the other element or intervening elements may be present therebetween. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Unless otherwise defined, all terms (including technical and scientific terms) used herein have the same meaning as commonly understood by one of ordinary skill in the art to which this invention belongs.

As used herein, "combination" is inclusive of blends, mixtures, alloys, reaction products, or the like.

As used herein, unless otherwise provided, the term "substituted" refers to that hydrogen in a compound, radical, or a functional group substituted with at least a substituent selected from a halogen (F, Cl, Br, or I), a hydroxyl group, an alkoxy group, a nitro group, a cyano group, an amino group, an azido group, an amidino group, a hydrazino group, hydrazono group, a carbonyl group, a carbamyl group, a thiol group, an ester group, a carboxyl group or salts thereof, a sulfonic acid group or salts thereof, a phosphoric acid group or salts thereof, a C1 to C20 alkyl group, a C2 to C16 alkenyl group a C2 to C16 alkynyl group, a C6 to C20 aryl group, a C7 to C13 arylalkyl group, a C1 to C4 alkoxy group, a C1 to C20 heteroalkyl group, a C3 to C20 heteroarylalkyl group, a C3 to C20 cycloalkyl group, a C3 to C15 cycloalkenyl group, a C6 to C15 cycloalkynyl group, a C3 to C15 heterocycloalkyl group, or a combination thereof, provided that the substituted atom's normal valence is not exceeded.

"Alkyl" refers to a straight or branched chain saturated aliphatic hydrocarbon group having the specified number of carbon atoms, specifically 1 to 12 carbon atoms, more specifically 1 to 6 carbon atoms. Alkyl groups include, for example, groups having from 1 to 50 carbon atoms (C1 to C50 alkyl).

"Aryl" refers to a cyclic moiety in which all ring members are carbon and at least one ring is aromatic. More than one ring may be present, and any additional rings may be the same or different aromatic, saturated or partially unsaturated, and may be fused, pendant, spirocyclic, or a combination thereof.

"Alkenyl" refers to a straight or branched chain hydrocarbon that has at least one carbon-carbon double bond.

"Akynyl" refers to a straight or branched chain hydrocarbon that has at least one carbon-carbon triple bond.

"Alkoxy" refers to an alkyl moiety that is linked via an oxygen (i.e., —O-alkyl). Non-limiting examples of C1 to C30 alkoxy groups include methoxy groups, ethoxy groups, propoxy groups, isobutyloxy groups, sec-butyloxy groups, pentyloxy groups, iso-amyloxy groups, and hexyloxy groups.

"Alkylene" refers to a straight, branched or cyclic divalent aliphatic hydrocarbon group, and may have from 1 to about 18 carbon atoms, more specifically 2 to about 12 carbons. One or more —CH$_2$— groups may be substituted with an ether group. Exemplary alkylene groups include methylene (—CH$_2$—), ethylene (—CH$_2$CH$_2$—), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—).

"Arylene" refers to a divalent radical formed by the removal of two hydrogen atoms from one or more rings of an aromatic hydrocarbon, wherein the hydrogen atoms may be removed from the same or different rings (preferably different rings), each of which rings may be aromatic or nonaromatic.

"Arylalkyl" group refers to an aryl group linked via an alkylene moiety. The specified number of carbon atoms (e.g., C7 to C30) refers to the total number of carbon atoms present in both the aryl and the alkylene moieties. Representative arylalkyl groups include, for example, benzyl groups.

"Aryloxy" refers to an aryl moiety that is linked via an oxygen (i.e., —O-aryl).

"Alkoxylene" group refers to an alkylene group linked via an oxygen (i.e., —O-alkylene).

"Amide" group refers to a group of the formula —C(O)—N(Rx)- wherein Rx is hydrogen, an alkyl, alkenyl, alkynyl, cycloalkyl or aryl group.

As used herein, unless otherwise provided, the term "hetero" refers to a group including 1 to 3 heteroatoms of N, O, S, Si, or P in a ring.

As used herein, unless otherwise provided, the term "alicyclic group" refers to a C3 to C30 cycloalkyl group, a C3 to C30 cycloalkenyl group, a C3 to C30 cycloalkynyl group, a C3 to C30 heterocycloalkyl group, a C3 to C30 heterocycloalkenyl group, a C3 to C30 heterocycloalkynyl group, or the like.

As used herein, unless otherwise provided, the term "aromatic cyclic group" refers to a cyclic structure in which unsaturated bonds, lone pairs, and the like are mixed, to provide a functional group in which the electrons are delocalized or resonated. Examples of the aromatic cyclic group include a C6 to C30 aryl group, a C2 to C30 heteroaryl group, and a C2 to C30 heterocycloalkenyl group.

According to an embodiment, provided is a liquid crystalline thermoset oligomer or polymer having increased heat resistance and mechanical properties by including a thermosetting cross-linking group at a side chain or a terminal end, and having improved flame retardancy and adherence by introducing a phosphorus-containing functional group at a main chain or a side chain.

The liquid crystalline thermoset oligomer or polymer may include a structural unit of the following Chemical Formulae 1 and 2, and may include a functional group of Chemical Formula A at at least one terminal end.

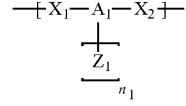
[Chemical Formula 1]

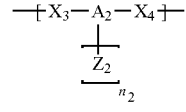
[Chemical Formula 2]

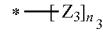
[Chemical Formula A]

In Chemical Formulae 1, 2, and A, $X_1$ to $X_4$ are the same or different, and are C(=O)O, O, C(=O)NR, NR', or CO, wherein R and R' are the same or different, and are hydrogen, a substituted or unsubstituted C1 to C20 alkyl group, or a substituted or unsubstituted C6 to C30 aryl group, $Z_1$ to $Z_3$ are the same or different, and are a hydroxyl group; a thiol group; a substituted or unsubstituted maleimide group; a substituted or unsubstituted nadimide group; a substituted or unsubstituted tetrahydrophthalimide group a substituted or unsubstituted C2 to C30 alkenyl group; a substituted or unsubstituted C2 to C30 alkynyl group; a substituted or unsubstituted propargyl ether group; a substituted or unsubstituted benzocyclobutene group; an (iso)cyanate group; a cyanide group; a substituted or unsubstituted C3 to C30 alicyclic group including a double bond or a triple bond; a substituted or unsubstituted heteroatom-containing C3 to C30 alicyclic group including a double bond or a triple bond; a C3 to C30 alicyclic group including a C2 to C30 alkenyl group or a C2 to C30 alkynyl group; a heteroatom-containing C3 to C30 alicyclic group including a C2 to C30 alkenyl group or a C2 to C30 alkynyl group; a C6 to C30 aryl group including a C2 to C30 alkenyl group or a C2 to C30 alkynyl group; a C6 to C30 aryl group including an (iso)cyanate group or a cyanide group; or a combination thereof, and n1 to n3 are the same or different, and are integers ranging from 0 to about 3, and the sum n1+n2+n3 is 1 or more.

In Chemical Formula 1, $A_1$ is a functional group represented by the following Chemical Formulae 4-1 to 4-7. $A_1$ may be an aromatic ring linked to a main chain at an ortho or a meta position of the aromatic ring. Such an aromatic moiety may have a kink structure, and may be repeatedly introduced to the liquid crystalline thermoset oligomer or polymer main chain. When the kink structure is introduced, the linearity of the liquid crystalline thermoset oligomer or polymer main chain is decreased, and therefore interactions between the main chains and crystallinity are decreased, and properties, such that solubility in a solvent, may be improved.

[Chemical Formula 4-1]

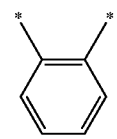

[Chemical Formula 4-2]

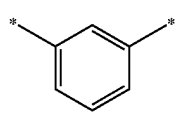

[Chemical Formula 4-3]

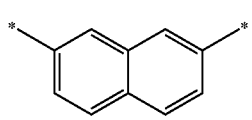

[Chemical Formula 4-4]

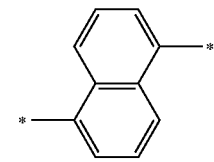

[Chemical Formula 4-5]

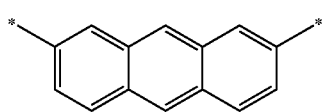

[Chemical Formula 4-6]

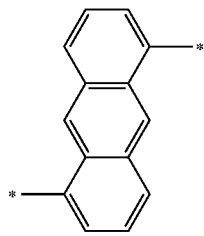

[Chemical Formula 4-7]

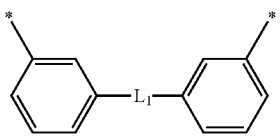

In Chemical Formula 4-7, $L_1$ is a divalent substituted or unsubstituted hydrocarbon (e.g., organic functional) group, in Chemical Formulae 4-1 to 4-7, at least one hydrogen of each aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$ (wherein $Z_1$ is the same as defined in Chemical Formula 1).

$A_2$ of Chemical Formula 2 is a functional group represented by the following Chemical Formulae 5-1 to 5-6, or a C2 to C20 alkylene group including a functional group of the following Chemical Formula 6.

[Chemical Formula 5-1]

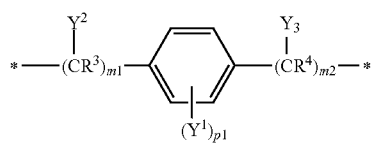

In Chemical Formula 5-1, $Y^1$ to $Y^3$ are the same or different, and are hydrogen, a C1 to C10 alkyl group, or a functional group represented by the following Chemical Formula 6, provided that at least one of $Y^1$ to $Y^3$ is the functional group represented by the following Chemical Formula 6, p1 is an integer ranging from 0 to 4, m1 and m2 are the same or different, and are integers ranging from 0 to 3, provided that p1, m1, and m2 are not simultaneously zero (0), and $R^3$ and $R^4$ are the same or different, and are hydrogen or a C1 to C10 alkyl group.

[Chemical Formula 5-2]

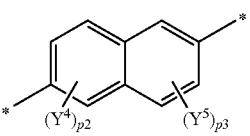

In Chemical Formula 5-2, $Y^4$ and $Y^5$ are the same or different, and are hydrogen, a C1 to C10 alkyl group, or a functional group represented by the following Chemical Formula 6, provided that at least one of $Y^4$ and $Y^5$ is the functional group represented by the following Chemical Formula 6, and p2 and p3 are the same or different, and are integers ranging from 0 to 3, provided that p2 and p3 are not simultaneously zero (0).

[Chemical Formula 5-3]

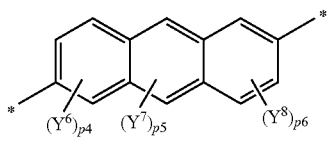

In Chemical Formula 5-3, $Y^6$ to $Y^8$ are the same or different, and are hydrogen, a C1 to C10 alkyl group, or a functional group represented by the following Chemical Formula 6, provided that at least one of $Y^6$ to $Y^8$ is the functional group represented by the following Chemical Formula 6, and p4 and p6 are the same or different, and are integers ranging from 0 to 3, and p5 is an integer ranging from 0 to 2, provided that p4, p5, and p6 are not simultaneously zero (0).

[Chemical Formula 5-4]

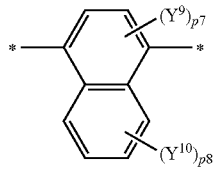

In Chemical Formula 5-4, $Y^9$ and $Y^{10}$ are the same or different, and are hydrogen, a C1 to C10 alkyl group, or a functional group represented by the following Chemical Formula 6, provided that at least one of $Y^9$ and $Y^{10}$ is the functional group represented by the following Chemical Formula 6, and p7 and p8 are the same or different, and are integers ranging from 0 to 2, provided that p7 and p8 are not simultaneously zero (0).

[Chemical Formula 5-5]

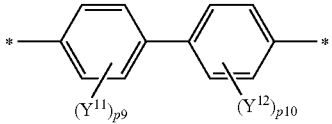

In Chemical Formula 5-5, $Y^{11}$ and $Y^{12}$ are the same or different, and are hydrogen, a C1 to C10 alkyl group, or a functional group represented by the following Chemical Formula 6, provided that at least one of $Y^{11}$ and $Y^{12}$ is the functional group represented by the following Chemical Formula 6, and p9 and p10 are the same or different, and are integers ranging from 0 to 4, provided that p9 and p10 are not simultaneously zero (0).

[Chemical Formula 5-6]

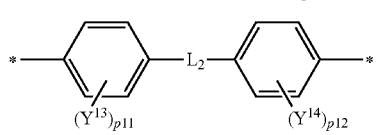

In Chemical Formula 5-6, $Y^{13}$ and $Y^{14}$ are the same or different, and are hydrogen, a C1 to C10 alkyl group, or a functional group represented by the following Chemical Formula 6, provided that at least one of $Y^{13}$ and $Y^{14}$ is the functional group represented by the following Chemical Formula 6, p11 and p12 are the same or different, and are integers ranging from 0 to 4, and $L_2$ is an ether group, a sulfide group, a ketone group, an amide group, a sulfoxide group, a sulfone group, an azo group, an imine group, a substituted or unsubstituted C1 to C20 alkylene group, a substituted or unsubstituted C2 to C20 alkenylene group, a substituted or unsubstituted C6 to C30 arylene group, a divalent hydrocarbon (e.g., organic functional) group that is unsubstituted or substituted with at least one functional group represented by Chemical Formula 6, or a divalent hydrocarbon (e.g., organic functional) group of Chemical Formulae 7-1 to 7-3, provided that both p11 and p12 are not zero (0) when $L_2$ is unsubstituted with a functional group of the following Chemical Formula 6.

In Chemical Formulae 5-1 to 5-6, or alternatively in Chemical Formula 4-1 to Chemical Formula 4-7 and in Chemical Formula 5-1 to 5-6, at least one hydrogen of each aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$ (wherein $Z_1$ is the same as defined in Chemical Formula 1).

[Chemical Formula 6]

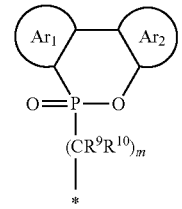

In Chemical Formula 6, $Ar_1$ and $Ar_2$ are the same or different, and are a C4 to C30 substituted or unsubstituted aromatic cyclic group, $R^9$ and $R^{19}$ are the same or different, and are hydrogen, a C1 to C20 alkyl group, or a C6 to C30 aryl group, and m is an integer ranging from 0 to about 3.

[Chemical Formula 7-1]

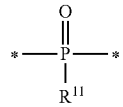

In Chemical Formula 7-1, $R^{11}$ is hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group.

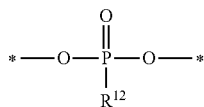
[Chemical Formula 7-2]

In Chemical Formula 7-2,
$R^{12}$ is hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group.

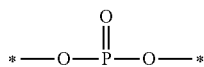
[Chemical Formula 7-3]

The liquid crystalline thermoset oligomer has a number average molecular weight of about 500 to about 10,000 grams per mole (g/mol), specifically 1000 to about 9,000 g/mol, more specifically 2000 to about 8,000 g/mol, and the liquid crystalline thermoset polymer has a number average molecular weight of about 10,000 to about 1,000,000 g/mol, specifically 20,000 to about 800,000 g/mol, more specifically 30,000 to about 700,000 g/mol. When the liquid crystalline thermoset oligomer or polymer has a number average molecular weight within the foregoing range, it may have a desirable cross-linking density, and it may also provide excellent properties due to excellent solubility in a solvent and may include enough solid content during impregnation in a net structure for preparing a prepreg.

The structural unit of Chemical Formula 1 may be included in an amount of about 5 mol % to about 60 mol %, specifically about 10 mol % to about 50 mol %, more specifically about 15 mol % to about 40 mol %, based on the total amount of the liquid crystalline thermoset oligomer or polymer, and the structural unit of Chemical Formula 2 may be included in an amount of about 40 mol % to about 95 mol %, specifically about 50 mol % to about 90 mol %, more specifically about 60 mol % to about 80 mol % based on the total amount of the liquid crystalline thermoset oligomer or polymer. When the structural units of Chemical Formulae 1 and 2 are included within the foregoing range, a solubility of the liquid crystalline thermoset oligomer or polymer may be improved.

The liquid crystalline thermoset oligomer or polymer may further include a structural unit of the following Chemical Formula 3.

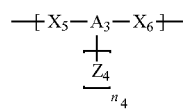
[Chemical Formula 3]

In Chemical Formula 3,
$X_5$ to $X_6$ are the same or different, and are C(=O)O, O, C(=O)NR, NR', or CO (wherein R and R' are the same or different, and are hydrogen, a substituted or unsubstituted C1 to C20 alkyl group, or a substituted or unsubstituted C6 to C30 aryl group), $Z_4$ is a hydroxyl group; a thiol group; a substituted or unsubstituted maleimide group; a substituted or unsubstituted nadimide group; a substituted or unsubstituted tetrahydrophthalimide group; a substituted or unsubstituted C2 to C30 alkenyl group; a substituted or unsubstituted C2 to C30 alkynyl group; a substituted or unsubstituted propargyl ether group; a substituted or unsubstituted benzocyclobutene group; an (iso)cyanate group; a cyanide group; a substituted or unsubstituted C3 to C30 alicyclic group including a double bond or a triple bond; a substituted or unsubstituted heteroatom-containing C3 to C30 alicyclic group including a double bond or a triple bond; a C3 to C30 alicyclic group including a C2 to C30 alkenyl group or a C2 to C30 alkynyl group; a heteroatom-containing C3 to C30 alicyclic group including a C2 to C30 alkenyl group or a C2 to C30 alkynyl group; a C6 to C30 aryl group including a C2 to C30 alkenyl group or a C2 to C30 alkynyl group; a C6 to C30 aryl group including an (iso)cyanate group or a cyanide group; or a combination thereof, $n_4$ is an integer ranging from 0 to about 3, and
$A_3$ is a functional group represented by the following Chemical Formulae 5-7 to 5-12.

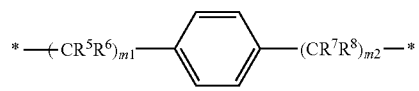
[Chemical Formula 5-7]

In Chemical Formula 5-7,
m1 and m2 are the same or different, and are integers ranging from 0 to about 3, and
$R^5$ to $R^8$ are the same or different, and are hydrogen or a C1 to C10 alkyl group.

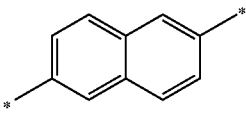
[Chemical Formula 5-8]

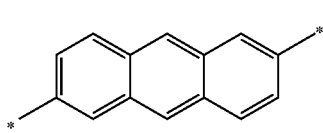
[Chemical Formula 5-9]

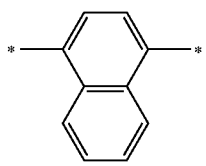
[Chemical Formula 5-10]

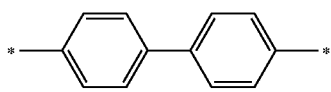
[Chemical Formula 5-11]

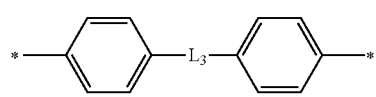
[Chemical Formula 5-12]

In Chemical Formula 5-12,
$L_3$ is the same as $L_1$ of Chemical Formula 4-7.

In Chemical Formulae 5-7 to 5-12, at least one hydrogen of each aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$, wherein $Z_1$ is the same as defined in Chemical Formula 1.

The structural unit of Chemical Formula 3 may be included in an amount of about 0.01 to about 20 moles, specifically about 0.1 to about 15 moles, more specifically about 1 to about 10 moles, based on 1 mol of structural unit of Chemical Formula 2. When the structural unit is included within the foregoing range, the liquid crystalline thermoset oligomer or polymer may provide improved flame retardancy.

The liquid crystalline thermoset oligomer may include one or more of the same or different thermosetting cross-linking groups at the terminal or side chain. Without being bound by theory, it is believed that the thermosetting cross-linking group provides a stable structure having a rigid net structure through cross-linking reactions between thermosetting functional groups through promoted by curing at a high temperature when a thermosetting composition is used for fabricating a flexible printed circuit ("FPC"). Thereby, a flexible printed circuit ("FPC") may have improved mechanical properties. Further, a film fabricated using the thermosetting composition and cross-linking reactions between the cross-linking groups may have a high glass transition temperature and a low coefficient of thermal expansion.

$Z_1$ to $Z_3$ may be a thermosetting cross-linking group represented by the following Chemical Formulae 8-1 to 8-7.

[Chemical Formula 8-1]

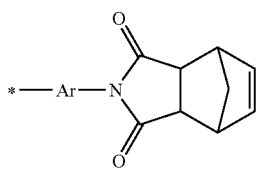

[Chemical Formula 8-2]

[Chemical Formula 8-3]

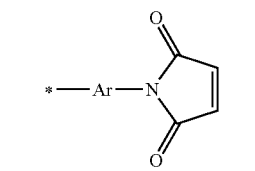

[Chemical Formula 8-4]

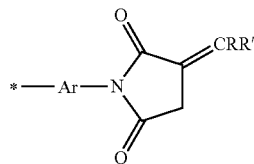

[Chemical Formula 8-5]

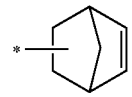

[Chemical Formula 8-6]

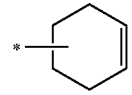

In Chemical Formulae 8-1 to 8-4, Ar is a C6 to C30 arylene group, and in Chemical Formula 8-4, R and R' are the same or different, and are hydrogen, a substituted or unsubstituted C1 to C20 alkyl group, or a substituted or unsubstituted C6 to C30 aryl group, and in Chemical Formulae 8-1 to 8-6, at least one hydrogen of each alicyclic ring or an aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group.

[Chemical Formula 8-7]

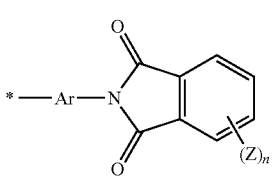

In Chemical Formula 8-7,

Ar is a C6 to C30 arylene group,

Z is a substituted or unsubstituted C2 to C20 alkenyl group, a substituted or unsubstituted C2 to C20 alkynyl group, or a substituted or unsubstituted C3 to C20 cycloalkenyl group, and n is an integer ranging from 1 to about 4, and at least one hydrogen of the aromatic ring may be unsubstituted or substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group.

$L_1$ of Chemical Formula 4-7 may be an ether group, a sulfide group, a ketone group, a sulfoxide group, a sulfone group, an azo group, an imine group, a substituted or unsubstituted C1 to C20 alkylene group, a substituted or unsubstituted C2 to C20 alkenylene group, a substituted or unsubstituted C6 to C30 arylene group, or a combination comprising at least one of the foregoing. $L_1$ may be one of the following Chemical Formulae 9-1 to 9-10.

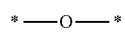

[Chemical Formula 9-1]

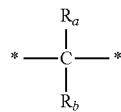

[Chemical Formula 9-2]

In Chemical Formula 9-2, $R_a$ and $R_b$ are the same or different, and are hydrogen, a halogen, a C1 to C5 alkyl group, a C1 to C5 haloalkyl group, or $Z_1$, wherein $Z_1$ is the same as defined in Chemical Formula 1.

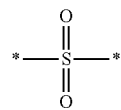

[Chemical Formula 9-3]

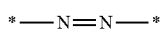

[Chemical Formula 9-4]

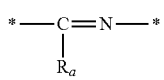

[Chemical Formula 9-5]

In Chemical Formula 9-5, $R_a$ is hydrogen, a halogen, a C1 to C5 alkyl group, a C1 to C5 haloalkyl group, or $Z_1$, wherein $Z_1$ is the same as defined in Chemical Formula 1.

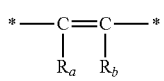

[Chemical Formula 9-6]

In Chemical Formula 9-6, $R_a$ and $R_b$ are the same or different and are hydrogen, a halogen, a C1 to C5 alkyl group, a C1 to C5 haloalkyl group, or $Z_1$, wherein $Z_1$ is the same as defined in Chemical Formula 1.

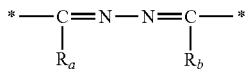

[Chemical Formula 9-7]

In Chemical Formula 9-7, $R_a$ and $R_b$ are the same or different and are hydrogen, a halogen, a C1 to C5 alkyl group, a C1 to C5 haloalkyl group, or $Z_1$, wherein $Z_1$ is the same as defined in Chemical Formula 1.

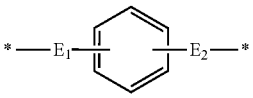

[Chemical Formula 9-8]

In Chemical Formula 9-8, $E_1$ and $E_2$ are the same or different, are a linking group, and are a single bond, an ether group, an ester group, a ketone group, a sulfide group, a sulfoxide group, a sulfone group, or a combination comprising at least one of the foregoing.

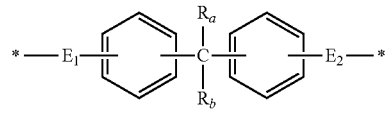

[Chemical Formula 9-9]

In Chemical Formula 9-9, $R_a$ and $R_b$ are the same or different, and are hydrogen, a halogen, a C1 to C5 alkyl group, a C1 to C5 haloalkyl group, or $Z_1$, wherein $Z_1$ is the same as defined in Chemical Formula 1, and $E_1$ and $E_2$ are the same or different, and are a linking group, and are a single bond, an ether group, an ester group, a ketone group, a sulfide group, a sulfoxide group, a sulfone group, or a combination comprising at least one of the foregoing.

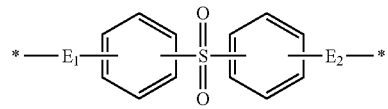

[Chemical Formula 9-10]

In Chemical Formula 9-10, $E_1$ and $E_2$ are the same or different linking group, and are a single bond, an ether group, an ester group, a ketone group, a sulfide group, a sulfoxide group, or a sulfone group.

In Chemical Formulae 9-8 to 9-10, at least one hydrogen of each aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$, wherein $Z_1$ is the same as defined in Chemical Formula 1.

$L_2$ of Chemical Formula 5-6 is an ether group, a sulfide group, a ketone group, an amide group, a sulfoxide group, a sulfone group, an azo group, an imine group, a substituted or unsubstituted C1 to C20 alkylene group, a substituted or unsubstituted C2 to C20 alkenylene group, a substituted or unsubstituted C6 to C30 arylene group, a divalent hydrocarbon (e.g., organic functional) group which is unsubstituted or substituted with a functional group represented by Chemical Formula 6, or is a divalent hydrocarbon (e.g., organic functional) group of Chemical Formulae 7-1 to 7-3.

$L_2$ may be a group according to Chemical Formulae 9-1 to 9-10. In Chemical Formulae 9-2, 9-5, 9-6, 9-7, and 9-9, $R_a$ and $R_b$ are the same or different, and are hydrogen, a halogen, a C1 to C5 alkyl group, a C1 to C5 haloalkyl group, $Z_1$, wherein $Z_1$ is the same as defined in Chemical Formula 1, or a functional group of Chemical Formula 6. In Chemical Formulae 9-8 to 9-10, at least one hydrogen of each aromatic ring may be substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$, wherein $Z_1$ is the same as defined in Chemical Formula 1, or a functional group of Chemical Formula 6.

Chemical Formula 6 may include the following Chemical Formula 11.

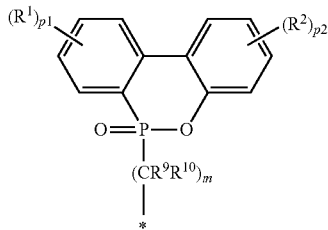

[Chemical Formula 11]

In Chemical Formula 11, $R^1$ and $R^2$ are the same or different, and are hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$, wherein $Z_1$ is the same as defined in Chemical Formula 1, p1 and p2 are integers ranging from 0 to 4, and $R^9$ and $R^{10}$ are the same or different, and are hydrogen, a C1 to C20 alkyl group, or a C6 to C30 aryl group, and m is an integer ranging from 0 to about 3.

According to another embodiment, a thermosetting composition including the liquid crystalline thermoset oligomer or polymer is provided.

The thermosetting composition may further include a solvent. The solvent may be a polar aprotic solvent. Examples of the polar aprotic solvent include a halogenated solvent, such as 1-chlorobutane, chlorobenzene, 1,1-dichloroethane, 1,2-dichloroethane, chloroform, 1,1,2,2-tetrachloroethane, or the like; an ether, such as diethylether, tetrahydrofuran, 1,4-dioxane, or the like; a ketone solvent such as methylethylketone ("MEK"), acetone, cyclohexanone, or the like; an acetate, such as propylene glycol monomethyl ether acetate ("PGMEA"); an ester, such as ethyl acetate, or the like; a lactone, such as γ-butyrolactone, or the like; a carbonate, such as ethylene carbonate, propylene carbonate, or the like; an amine, such as triethylamine, pyridine, or the like; a nitrile, such as acetonitrile, or the like; an amide, such as N,N-dimethyl formamide ("DMF"), N,N-dimethyl acetamide ("DMAc"), tetramethylurea, N-methylpyrrolidone ("NMP"), or the like; a nitro-substituted solvent such as nitromethane, nitrobenzene, or the like; a sulfide, such as dimethyl sulfoxide ("DMSO"), sulfolane, or the like; a phosphoric acid derivative, such as hexamethylphosphor amide, tri-n-butylphosphate, or the like; or a combination thereof, but is not limited thereto.

In an embodiment, the solvent may include N-methylpyrrolidone, dimethyl sulfoxide, N,N-dimethyl formamide, N,N-diethylformamide, N,N-dimethyl acetamide, N,N-dimethyl acetamide, N-methylpropionamide, N-methylcaprolactam, γ-butyrolactone, dimethylimidazolidinone, tetramethylphosphoric amide, ethylcellosolve acetate, methylethylketone, propylene glycol monomethyl ether acetate, or a combination thereof.

In an embodiment, the solvent may include N-methylpyrrolidone ("NMP"), dimethyl sulfoxide ("DMSO"), N,N-dimethyl formamide ("DMF"), N,N-dimethyl acetamide ("DMAc"), methylethylketone ("MEK"), propylene glycol monomethyl ether acetate ("PGMEA"), or a combination thereof.

In an embodiment, the thermosetting composition may include about 0.1 to about 300 parts by weight, specifically about 1 to about 200 parts by weight, more specifically about 10 to about 100 parts by weight of a liquid crystalline thermosetting oligomer or polymer, based on 100 parts by weight of a solvent.

The thermosetting composition may further include a maleimide cross-linking agent including two or more maleimide groups. The maleimide cross-linking agent may be bismaleimide, and may be represented by the following Chemical Formula 12.

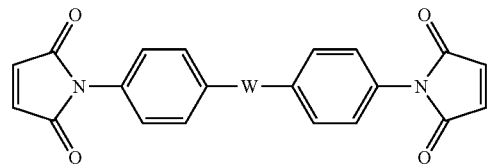

[Chemical Formula 12]

In Chemical Formula 12,

W is a single bond, an ether group, a sulfide group, a ketone group, a sulfoxide group, a sulfone group, a substituted or unsubstituted C1 to C20 alkylene group, a substituted or unsubstituted C2 to C20 alkoxylene group, a substituted or unsubstituted C6 to C30 arylene group, or a substituted or unsubstituted C6 to C30 (hetero)arylene group including at least one of an ether group, a sulfide group, a ketone group, a sulfoxide group, a sulfone group, an amide group, or an ester group.

The maleimide compound may function as a cross-linking agent by binding a thermosetting cross-linking group of the liquid crystalline thermoset oligomer or polymer.

The thermosetting composition may further include an epoxy compound. Examples of the epoxy compound include a phenol glycidylether-type epoxy resin, such as a phenol novolac-type epoxy resin, a cresol novolac-type epoxy resin, a naphthol modified novolac-type epoxy resin, a bisphenol A-type epoxy resin, a bisphenol F-type epoxy resin, a biphenyl-type epoxy resin, a triphenyl-type epoxy resin, or the like; a dicyclopentadiene-type epoxy resin having a dicyclopentadiene backbone; a naphthalene-type epoxy resin having a naphthalene backbone; a dihydroxybenzopyran-type epoxy resin; a glycidylamine-type epoxy resin made from polyamine such as diaminophenyl methane; a triphenolmethane-type epoxy resin; a tetraphenylethane-type epoxy resin; or a combination thereof.

The epoxy compound may be included in an amount of about 5 to about 40 parts by weight, specifically about 10 to about 35 parts by weight, more specifically about 15 to about 30 parts by weight, based on 100 parts by weight of the thermosetting composition. When the epoxy compound is included within the foregoing range, adherence between the thermosetting composition and copper and so on may be improved.

The thermosetting composition according to an embodiment may further include a polymer such as a thermosetting resin and a thermoplastic resin besides the liquid crystalline thermoset oligomer or polymer.

Examples of the polymer include a phosphorous compound such as phosphoric acid ester or phosphoric acid amide, for example melamine polyphosphate; a nitrogen-including compound such as melamine or benzoguanamine; an oxazine ring-including compound; a silicone compound; a polyimide; a polyvinylacetal; a phenoxy resin; an acryl resin; an acryl resin including a hydroxy or carboxyl group; an alkyd resin; elastomers such as a polyurethane resin, polybutadiene, a butadiene-acrylonitrile copolymer, polychloroprene, a butadiene-styrene copolymer, polyisoprene, a butyl rubber, a fluoro rubber, a natural rubber, a styrene-isoprene rubber, an acryl rubber, an epoxylated butadiene, and a maleated butadiene; polyethylene; polypropylene; a polyethylene-propylene copolymer; polyvinyl chloride; polyvinylidene chloride; polystyrene; polyvinyl toluene; polyvinyl phenol; an acrylonitrile styrene resin; an acrylonitrile butadiene styrene resin; a (meth)acrylate-butadiene-styrene resin; polytetrafluoroethylene, a fluoroethylene-propylene copolymer; a tetrafluoroethylene-hexafluoroethylene copolymer; polyvinylidene fluoride; polycarbonate; polyester carbonate; polyphenylene ether; polysulfone; polyester; polyether sulfone; polyamide; polyamide imide; polyester imide; polyphenylene sulfide; poly(meth)acrylate; polyepoxy (meth)acrylate; polydi(meth)acryloxy-bisphenol; poly (meth)acrylate, polystyrene, polyvinylpyrrolidone, polydiacryl phthalate, polydivinylbenzene, polydiallylbenzene; polydiallyl ether bisphenol; polytrialkenyl isocyanurate; polydicyclopentadiene; a phenolic resin; polyisocyanate; or the like, or a combination comprising at least one of the foregoing.

The thermosetting composition according to an embodiment further includes at least one additive such as a filler, a softening agent, a plasticizer, an antioxidant, a flame retardant, a flame-retardant aid, a lubricant, an antistatic agent, a colorant, a heat stabilizer, a light stabilizer, a UV absorber, a coupling agent, a precipitation inhibitor, or a combination comprising at least one of the foregoing.

The filler may include an organic filler, an inorganic filler, or a combination thereof. Non-limiting examples of the organic filler include epoxy resin powder, melamine resin powder, urea resin powder, benzoguanamine resin powder, a styrene resin powder, or the like, or a combination comprising at least one of the foregoing. Non-limiting examples of the inorganic filler include natural silica, fused silica, amorphous silica, hollow silica, aluminum hydroxide, boehmite, magnesium hydroxide, molybdenum oxide, zinc molybdate, zinc borate, zinc stannate, aluminum borate, potassium titanate, magnesium sulfate, silicon carbide, zinc oxide, silicon nitride, silicon dioxide, aluminum titanate, barium titanate, barium strontium titanate, aluminum oxide, alumina, clay, kaolin, talc, calcined clay, calcined kaolin, calcined talc, mica, short glass fiber, or the like, or a combination comprising at least one of the foregoing. The foregoing may be used singularly or as a mixture of two or more thereof.

Non-limiting examples of the plasticizer include polyethylene glycol, a polyamide oligomer, ethylene bis(stearo)amide, phthalate ester, a polystyrene oligomer, liquid paraffin, polyethylene wax, silicone oil, or the like, or a combination comprising at least one of the foregoing. The forgoing may be used singularly or as a mixture of two or more thereof.

Non-limiting examples of the antioxidant include a phosphorous-including antioxidant, a phenolic antioxidant, a sulfur-including antioxidant, or the like, or a combination comprising at least one of the foregoing. The foregoing may be used singularly or as a mixture of two or more thereof.

The thermosetting resin composition may be prepared by blending the components in accordance with various methods, such as mixing at room temperature or melt-mixing the same.

The thermosetting composition may be cast on a board to provide a thin film and cured at high temperature. The thermosetting composition may be filtered using a filter, and impurities included in the solution may be removed before being coated or impregnated.

When the board is prepared using the thermosetting composition, the heat resistance of the board may be improved and the dielectric constant of the board may be lowered. Further, the thermosetting composition including an oligomer or polymer having a phosphorus-containing functional group at the main chain or the side chain does not undergo phase separation and may have more improved adhesion than a thermosetting composition including a flame retardant separately.

According to another embodiment, a prepreg prepared using the thermosetting composition is provided.

The prepreg may be fabricated by coating or impregnating a reinforcing material with the thermosetting composition, curing, and then drying the same to remove the solvent. The impregnation may include dip coating, roll coating, or the like. Non-limiting examples of the reinforcing material include woven glass fiber, woven alumina glass fiber, a non-woven glass fiber fabric, a non-woven cellulose fabric, woven carbon fiber, polymer fabrics, or the like, or a combination comprising at least one of the foregoing. In addition, the reinforcing material may include a glass fiber, a silica glass fiber, a carbon fiber, an alumina fiber, a silicon carbide fiber, asbestos, rock wool, mineral wool, plaster whisker, a woven or non-woven fabric thereof, an aromatic polyamide fiber, a polyimide fiber, a liquid crystal polyester, a polyester fiber, a fluorine fiber, a polybenzoxazole fiber, a glass fiber including a polyamide fiber, a glass fiber including a carbon fiber, a glass fiber including a polyimide fiber, a glass fiber including an aromatic polyester, a glass paper, a mica paper, an alumina paper, a craft paper, a cotton paper, a paper-glass bond paper, or the like, or a combination comprising at least one of the foregoing. The foregoing may be used singularly or as a mixture of two or more thereof. The glass fiber may have a thickness of about 5 to about 200 micrometers ($\mu m$), specifically about 10 to about 180 $\mu m$, more specifically about 15 to about 160 $\mu m$. The thermosetting composition may be impregnated in an amount of about 0.4 to about 3 parts by weight, specifically about 0.5 to about 2.5 parts by weight, more specifically about 1 to about 2 parts by weight, based on 1 part by weight of the reinforcing material. When the thermosetting composition is impregnated within the foregoing range and two or more prepregs are used, adhesion between prepregs is improved, and the mechanical strength and dimensional stability of a prepreg are improved. The cure may be performed at a temperature of about 150 to about 350° C., specifically about 160 to about 300° C., more specifically about 170 to about 250° C., and a flexible printed circuit ("FPC") may be provided through heat-treatment at a relatively low temperature as described above.

The prepreg may be bound with copper. Alternatively, the thermosetting resin composition may be impregnated in the reinforcing material, a heat treatment process may be performed at a semi-cured phase to provide a prepreg, and then the prepreg may be positioned on a copper foil followed by heat treatment. A copper and prepreg combined member may be prepared during a solvent removal and heat treatment process. In order to evaporate the solvent, it may be heated under a reduced pressure or may be ventilated. The coating of the thermosetting composition may be performed by roller coating, dip coating, spray coating, spin coating, curtain coating, slit coating, screen printing, or the like, but is not limited thereto.

The thermosetting composition solution may be used to fabricate a film. For example, a film is fabricated by forming a thermosetting composition solution layer through a solvent casting method, and removing the solvent from the thermosetting composition solution layer. The board may include a metal foil such as a copper foil, an aluminum foil, a gold foil, a silver foil, or a glass board, a PET film, or the like, or a combination comprising at least one of the foregoing.

According to yet another embodiment, a flexible printed circuit ("FPC") prepared using the thermosetting composition is provided. The FPC may include a film, a printed board, a copper clad laminate, a prepreg, or a combination thereof. Also, the FPC may be a copper clad laminate ("CCL") or a flexible copper clad laminate.

The FPC may include the prepreg, and the FPC may be fabricated by laminating a metal layer on the prepreg and melting and curing the prepreg in a press by pressing and heating. The metal layer may include copper, aluminum, iron, stainless steel, nickel, or the like, and it may include an alloy thereof. In addition, the FPC may include a metal layer on a plurality of surfaces of the prepreg, or the FPC may comprise a plurality of laminated prepregs. The FPC including the prepreg may be varied in many different ways. A surface or a plurality of surfaces of the FPC may be formed with a conductor pattern, and the conductor pattern may be formed in 4 layers or 8 layers of a multi-layer structure.

Hereinafter, this disclosure is illustrated in more detail with reference to examples. However, they are exemplary embodiments and are not limiting.

SYNTHESIS EXAMPLE 1

Preparation of Liquid Crystalline Thermoset Oligomer with Nadimide-Terminal End

A quantity of 32.739 grams (g) (0.30 mol) of 4-aminophenol, 24.920 g (0.15 mol) of isophthalic acid, 40.607 g (0.294 mol) of 4-hydroxybenzoic acid, 55.325 g (0.294 mol) of 6-hydroxy-2-naphthoic acid, 84.984 g (0.30 mol) of 4-nadimidobenzoic acid, and 134 g (1.307 mol) of acetic anhydride are put into a 500 milliliter (ml) 4-neck flask. The flask is equipped with a hermetically sealed mechanical agitator, a nitrogen injection tube, a thermometer, and a reflux condenser. The internal air of the reactor is sufficiently substituted with nitrogen gas, and the temperature inside the reactor is gradually increased to about 140° C. under the flow of the nitrogen gas. Then, reflux is performed for about 3 hours while maintaining the reactor to have an internal temperature of about 140° C.

After an acetylation reaction is terminated, the internal temperature of the reactor is increased to about 200° C. while acetic acid and unreacted acetic anhydride, which are byproducts to be removed, are distilled. A liquid crystalline thermoset oligomer represented by the following Chemical Formula 13 is acquired by performing polymerization by heating the reactor for about 3 hours under the conditions and then additionally performing polymerization while evacuating the reactor for about 30 minutes. The liquid crystalline thermoset oligomer has a number average molecular weight (Mn) of 1010.

[Chemical Formula 13]

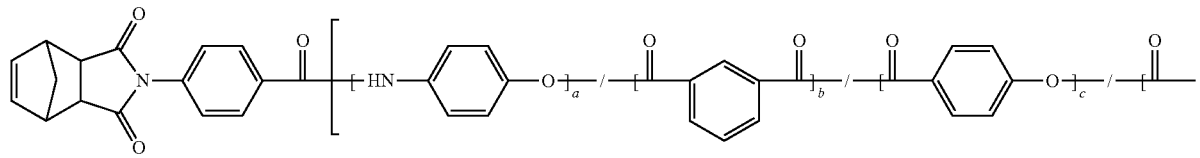

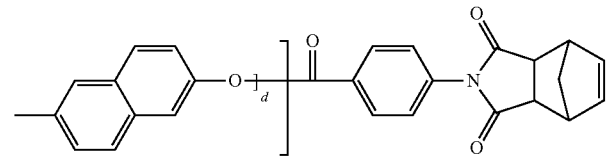

In Chemical Formula 13, a, b, c, and d represent a mole ratio of each structural unit, respectively, and are determined according to amounts of starting materials.

SYNTHESIS EXAMPLE 2

Preparation of Phosphorous-Including Liquid Crystalline Thermoset Oligomer with Capped Nadimide-Terminal End An amount of 16.369 g (0.15 mol) of 4-aminophenol, 24.920 g (0.15 mol) of isophthalic acid, 40.607 g (0.294 mol) of 4-hydroxybenzoic acid, 55.325 g (0.294 mol) of 6-hydroxy-2-naphthoic acid, 84.984 g (0.30 mol) of 4-nadimidobenzoic acid, 48.640 g (0.15 mol) of 2-(6-oxido-6H-dibenz[c.e][1,2]oxaphosphorin-6-yl)-1,4-benzenediol ("DOPO-HQ"), and 134 g (1.307 mol) of acetic anhydride are put into a 500 ml 4-neck flask.

The reaction conditions are the same as the reaction conditions of Synthesis Example 1, and a liquid crystalline thermoset oligomer represented by the following Chemical Formula 14 is acquired as a product. The liquid crystalline thermoset oligomer has a number average molecular weight (Mn) of 1490.

[Chemical Formula 14]

In Chemical Formula 14, a, b, c, d, and e represent a mole ratio of each structural unit, respectively, and are determined according to amounts of starting materials.

SYNTHESIS EXAMPLE 3

Preparation of Liquid Crystalline Thermoset Oligomer

A quantity of 16.369 g (0.15 mol) of 4-aminophenol, 24.920 g (0.15 mol) of isophthalic acid, 40.607 g (0.294 mol) of 4-hydroxybenzoic acid, 55.325 g (0.294 mol) of 6-hydroxy-2-naphthoic acid, 81.381 g (0.30 mol) of tetrahydrophthimidobenzoic acid, 48.640 g (0.15 mol) of DOPO-HQ, and 134 g (1.307 mol) of acetic anhydride are put into a 500 ml 4-neck flask.

The reaction conditions are the same as the reaction conditions of Synthesis Example 1, and a liquid crystalline thermoset oligomer represented by the following Chemical Formula 15 is acquired as a product. The liquid crystalline thermoset oligomer has a number average molecular weight (Mn) of 1430.

[Chemical Formula 15]

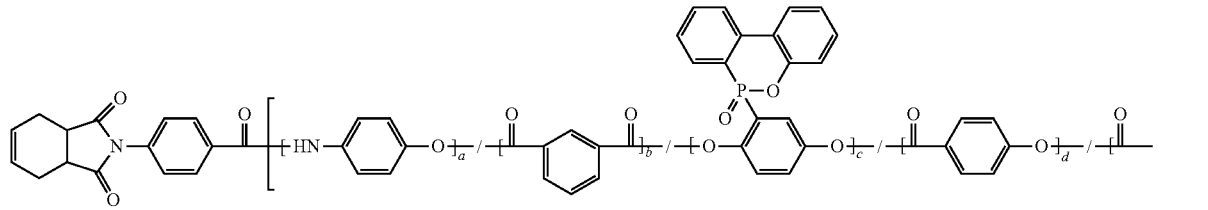

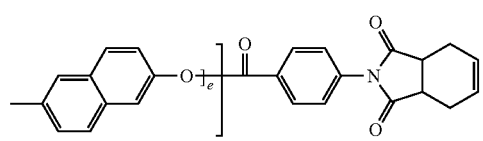

In Chemical Formula 15, a, b, c, d, and e represent a mole ratio of each structural unit, respectively, and are determined according to amounts of starting materials.

SYNTHESIS EXAMPLE 4

Preparation of Liquid Crystalline Thermoset Oligomer with Capped Hydroxyl Group-Terminal End A quantity of 65.478 g (0.60 mol) of 4-aminophenol, 74.759 g (0.45 mol) of isophthalic acid, 48.273 g (0.35 mol) of 4-hydroxybenzoic acid, 23.43 g (0.13 mol) of 6-hydroxy-2-naphthoic acid, and 190 g (1.84 mol) of acetic anhydride are put into a 500 ml 4-neck flask. The flask is equipped with a hermetically sealed mechanical agitator, a nitrogen injection tube, a thermometer, and a reflux condenser. The internal air of the reactor is sufficiently substituted with nitrogen gas, and the temperature inside the reactor is gradually increased to about 140° C. under the flow of the nitrogen gas. Then, reflux is performed for about 3 hours while maintaining the reactor to have an internal temperature of about 140° C. Next, a liquid crystalline thermoset oligomer including a hydroxyl group represented by the following Chemical Formula 16 is acquired by adding 42.340 g (0.23 mol) of 6-hydroxy-2-naphthoic acid and removing acetic acid and unreacted acetic anhydride, wherein during the reaction, the reacting temperature is increased to 270° C., and the reaction is performed for 30 minutes. The liquid crystalline thermoset oligomer has a number average molecular weight (Mn) of 1260.

SYNTHESIS EXAMPLE 5

Preparation of Phosphorous-Including Liquid Crystalline Thermoset Oligomer with Capped Hydroxyl Group-Terminal End A quantity of 49.108 g (0.45 mol) of 4-aminophenol, 74.759 g (0.45 mol) of isophthalic acid, 48.273 g (0.35 mol) of 4-hydroxybenzoic acid, 23.43 g (0.13 mol) of 6-hydroxy-2-naphthoic acid, 48.640 g (0.15 mol) of DOPO-HQ, and 190 g (1.84 mol) of acetic anhydride are put into a 500 ml 4-neck flask. The flask is equipped with a hermetically sealed mechanical agitator, a nitrogen injection tube, a thermometer, and a reflux condenser. The internal air of the reactor is sufficiently substituted with nitrogen gas, and the temperature inside the reactor is gradually increased to about 140° C. under the flow of the nitrogen gas. Then, reflux is performed for about 3 hours while maintaining the reactor to have an internal temperature of about 140° C. Next, a liquid crystalline thermoset oligomer including a hydroxyl group represented by the following Chemical Formula 17 is acquired by adding 42.340 g (0.23 mol) of 6-hydroxy-2-naphthoic acid, and removing acetic acid and unreacted acetic anhydride,

[Chemical Formula 16]

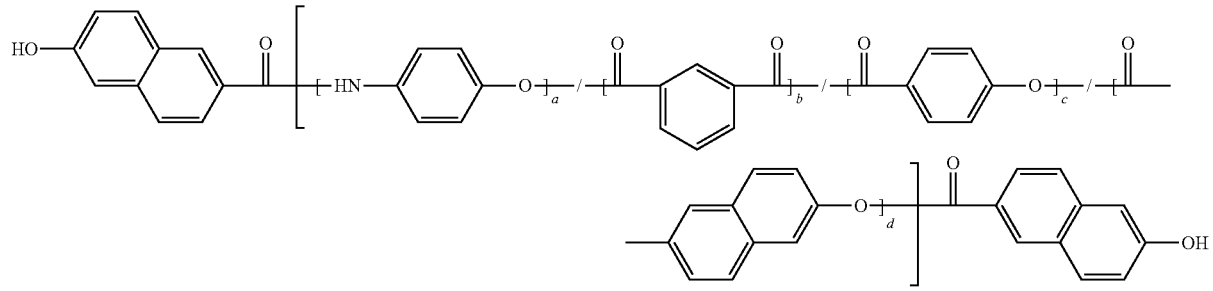

In Chemical Formula 16, a, b, c, and d represent a mole ratio of each structural unit, respectively, and are determined according to amounts of starting materials.

wherein during the reaction, the reacting temperature is increased to 270° C., and the reaction is performed for 30 minutes. The liquid crystalline thermoset oligomer has a number average molecular weight (Mn) of 1680.

[Chemical Formula 17]

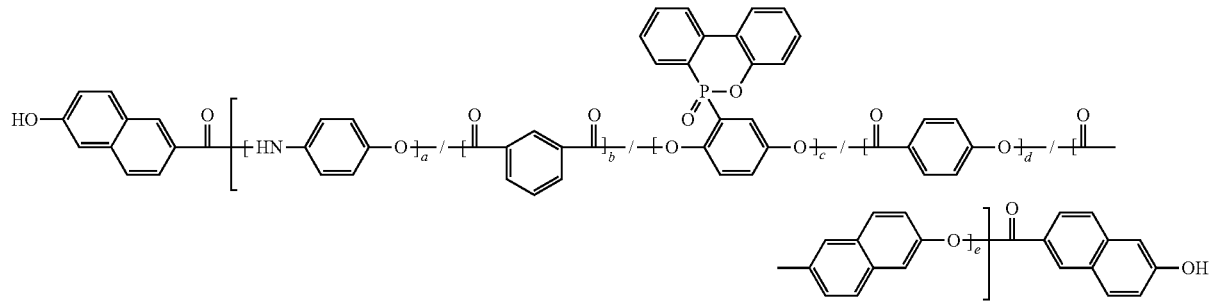

In Chemical Formula 17,
a, b, c, d, and e represent a mole ratio of each structural unit, respectively, and are determined according to amounts of starting materials.

EXAMPLE 1

Preparation of Prepreg

A mixture is prepared by putting 6.0 g of a liquid crystalline thermoset oligomer acquired from Synthesis Example 1, 6.0 g of a liquid crystalline thermoset oligomer acquired from Synthesis Example 5, 4.0 g of 4,4'-bismaleimidodiphenyl methane (BMI-1000, Daiwa Kasei company), 4.0 g of Araldite MY-721 (Huntsman company), and 0.04 g of a curing catalyst dicyandiamide ("DICY") into 30 g of N-methylpyrrolidone ("NMP"). Glass fiber 1078 (Nittobo company) is put on an electrodepositedelectrolytic copper foil fixed on a glass plate, and the prepared mixture is evenly impregnated into the glass fiber to provide a specimen. A prepreg is acquired by curing the specimen, which is impregnated for about 100 minutes, by increasing the temperature from room temperature to about 200° C. in a high-temperature furnace, and removing the copper foil by treating the cured specimen with 50 wt % of a nitric acid solution. Herein, the weight of the polymer based on the total weight of the prepreg is about 56 weight percent (wt %).

EXAMPLE 2

Preparation of Prepreg

A prepreg is provided according to the same method as Example 1, except that a mixture is prepared by putting 6.0 g of a oligomer acquired from Synthesis Example 2, 6.0 g of a oligomer acquired from Synthesis Example 4, 4.0 g of 4,4'-bismaleimidodiphenyl methane (BMI-1000, Daiwa Kasei company), 4.0 g of Araldite MY-721 (Huntsman company), and 0.04 g of a curing catalyst dicyandiamide ("DICY") into 30 g of N-methylpyrrolidone ("NMP"). Herein, the weight of the polymer based on the total weight of the prepreg is about 54 wt %.

EXAMPLE 3

Preparation of Prepreg

A prepreg is provided according to the same method as in Example 1, except that a mixed solution is prepared by putting 6.0 g of an oligomer acquired from Synthesis Example 2, 6.0 g of an oligomer acquired from Synthesis Example 5, 4.0 g of 4,4'-bismaleimidodiphenyl methane (BMI-1000, Daiwa Kasei company), 4.0 g of Araldite MY-721 (Huntsman company), and 0.04 g of a curing catalyst, dicyandiamide ("DICY"), into 30 g of N-methylpyrrolidone ("NMP"). Herein, the weight of the polymer based on the total weight of the prepreg is about 54 wt %.

EXAMPLE 4

Preparation of Prepreg

A prepreg is provided according to the same method as Example 1, except that a mixture is prepared by putting 12.0 g of a oligomer acquired from Synthesis Example 5, 4.0 g of 4,4'-bismaleimidodiphenyl methane (BMI-1000, Daiwa Kasei company), 4.0 g of Araldite MY-721 (Huntsman company), and 0.04 g of a curing catalyst dicyandiamide ("DICY") into 30 g of N-methylpyrrolidone ("NMP"). Herein, the weight of the polymer based on the total weight of the prepreg is about 56 wt %.

COMPARATIVE EXAMPLE 1

Preparation of Prepreg

A prepreg is provided according to the same method as Example 1, except that a mixed solution is prepared by putting 6.0 g of an oligomer acquired from Synthesis Example 1, 6.0 g of an oligomer acquired from Synthesis Example 4, 4.0 g of 4,4'-bismaleimidodiphenyl methane (BMI-1000, Daiwa Kasei company), 4.0 g of Araldite MY-721 (Huntsman company), and 0.04 g of a curing catalyst dicyandiamide ("DICY") into 30 g of N-methylpyrrolidone ("NMP"). Herein, the weight of the polymer based on the total weight of the prepreg is about 52 wt %.

COMPARATIVE EXAMPLE 2

Preparation of Prepreg

A prepreg is provided according to the same method as Example 1, except that a mixed solution is prepared by putting 6.0 g of an oligomer acquired from Synthesis Example 1, 6.0 g of an oligomer acquired from Synthesis Example 4, 4.0 g of 4,4'-bismaleimidodiphenyl methane (BMI-1000, Daiwa Kasei company), 4.0 g of Araldite MY-721 (Huntsman company), 1 g of DOPO-HQ, and 0.04 g of a curing catalyst, dicyandiamide ("DICY"), into 30 g of N-methylpyrrolidone ("NMP"). Herein, the weight of the polymer based on the total weight of the prepreg is about 52 wt %.

Evaluation of Thermal Property of Prepreg

Glass transition temperatures (Tg) and coefficients of thermal expansion ("CTE") of the prepreg specimens prepared according to Examples 1 to 4 and Comparative Examples 1 and 2 are measured with a thermomechanical analyzer ("TMA", TA Instruments TMA 2940), and the measurement results are presented in Table 1. The coefficients of thermal expansion ("CTE") are measured in the atmosphere of nitrogen while increasing the temperature at a rate of 10° C./minute. The measurement results of a coefficient of thermal expansion of a prepreg specimen according to Example 1 are shown in FIG. 1.

Evaluation of Peel Strength of Copper Foil

A copper foil is peeled in a width of about 1 centimeter (cm) from the surface of a copper foil laminate, and the peel strength of the copper foil is measured by using a tensile strength measuring instrument (Universal Testing machine). The test method is a 90 degree Peel Test, using a crosshead speed of 50 millimeters per minute (mm/min).

Evaluation of Flame Retardancy Properties

A copper foil laminate is fabricated by laminating 8 sheets of the semi-cured glass fiber prepreg prepared according to Examples 1 to 4 and Comparative Examples 1 and 2, disposing copper foil on both side of the prepreg laminate, and laminating the prepreg laminate with the copper foil. Then, the laminate is cured by using a press at 200° C. for about 100 minutes.

Flame retardancy is measured by the UL-94 standard evaluation method for flame retardancy using a rod-type specimen fabricated using the copper foil removed prepreg laminate, and are divided by V-0, V-1, and V-2 through a vertical burning test.

TABLE 1

|  | Ex. 1 | Ex. 2 | Ex. 3 | Ex. 4 | Comp. Ex. 1 | Comp. Ex. 2 |
|---|---|---|---|---|---|---|
| Glass transition temperature (° C.) | — | — | — | — | — | — |
| Coefficient of thermal expansion (ppm/° C.) | 15.9 | 16.3 | 17.1 | 15.1 | 14.6 | 15.0 |
| Peel strength (kgf/cm) | 0.92 | 0.94 | 0.90 | 0.94 | 0.91 | 0.50 |
| Flame retardancy UL94 | V-0 | V-0 | V-0 | V-0 | Fail | V-0 |

In Table 1, "ppm" refers to parts per million, and "kgf/cm" refers to kilograms force per centimeter.

As shown in the Table 1, the prepreg according to Examples 1 to 4 fabricated using the phosphorous-including liquid crystalline thermoset oligomer has a very low coefficient of thermal expansion ("CTE") and no glass transition temperature. Also, the prepreg fabricated using the phosphorous-including liquid crystalline thermoset oligomer has no change of adherence and has excellent flame retardancy compared to the prepreg fabricated according to Comparative Examples 1 and 2 using the non-phosphorous-including oligomer. The prepreg according to Comparative Example 2 using phosphorous as an additive ensure the flame retardancy, but the peel strength of the copper foil is deteriorated. Accordingly, when the prepreg according to Examples 1 to 4 were applied to a flexible printed circuit ("FPC"), the flexible printed circuit may have excellent electrical characteristics such as prevention of signal delay.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A liquid crystalline thermoset oligomer or polymer comprising:
   a structural unit of Chemical Formulae 1 and 2; and
   a functional group of Chemical Formula A at at least one terminal end,

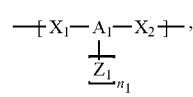

[Chemical Formula 1]

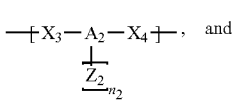

[Chemical Formula 2]

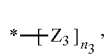

[Chemical Formula A]

wherein, in Chemical Formulae 1, 2, and A,
$X_1$ to $X_4$ are the same or different, and are C(=O)O, O, C(=O)NR, NR', or CO, wherein R and R' are the same or different, and are hydrogen, a substituted or unsubstituted C1 to C20 alkyl group, or a substituted or unsubstituted C6 to C30 aryl group,
$Z_1$ to $Z_3$ are the same or different, and are a hydroxyl group, a thiol group, a substituted or unsubstituted maleimide group, a substituted or unsubstituted nadimide group, a substituted or unsubstituted tetrahydrophthalimide group, a substituted or unsubstituted C2 to C30 alkenyl group, a substituted or unsubstituted C2 to C30 alkynyl group, a substituted or unsubstituted propargyl ether group, a substituted or unsubstituted benzocyclobutene group, an (iso)cyanate group, a cyanide group, a substituted or unsubstituted C3 to C30 alicyclic group including a double bond or a triple bond, a substituted or unsubstituted heteroatom-containing C3 to C30 alicyclic group including a double bond or a triple bond, a C3 to C30 alicyclic group including a C2 to C30 alkenyl group or a C2 to C30 alkynyl group, a heteroatom-containing C3 to C30 alicyclic group including a C2 to C30 alkenyl group or a C2 to C30 alkynyl group, a C6 to C30 aryl group including a C2 to C30 alkenyl group or a C2 to C30 alkynyl group, a C6 to C30 aryl group including an (iso)cyanate group or a cyanide group, or a combination thereof, $n_1$ to $n_3$ are the same or different integers ranging from 0 to about 3, and the sum $n_1+n_2+n_3$ is 1 or more, $A_1$ is a functional group represented by Chemical Formulae 4-1 to 4-7, and $A_2$ is a functional group represented by Chemical Formulae 5-1 to 5-6 or is a C2 to C20 alkylene group including a functional group represented by Chemical Formula 6,

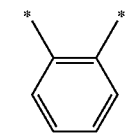

[Chemical Formula 4-1]

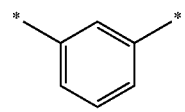

[Chemical Formula 4-2]

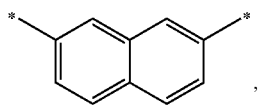

[Chemical Formula 4-3]

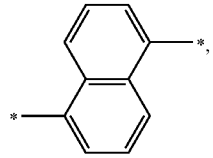

[Chemical Formula 4-4]

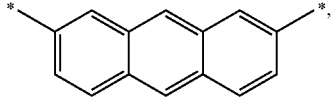

[Chemical Formula 4-5]

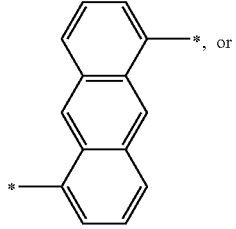

[Chemical Formula 4-6]

, or

-continued

[Chemical Formula 4-7]

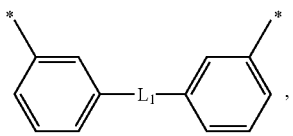

wherein, in Chemical Formula 4-7, $L_1$ is a divalent substituted or unsubstituted hydrocarbon group, wherein, in Chemical Formulae 4-1 to 4-7, at least one hydrogen of each aromatic ring is optionally substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$,

[Chemical Formula 5-1]

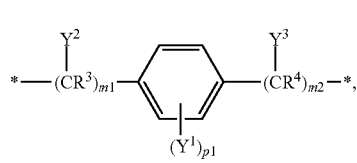

wherein, in Chemical Formula 5-1, $Y^1$ to $Y^3$ are the same or different, and are hydrogen, a C1 to C10 alkyl group, or a functional group represented by Chemical Formula 6, provided that at least one of $Y^1$ to $Y^3$ is a functional group represented by Chemical Formula 6, p1 is an integer ranging from 0 to 4, m1 and m2 are the same or different, and are integers ranging from 0 to about 3, provided that p1, m1, and m2 are not simultaneously zero, and $R^3$ and $R^4$ are the same or different and are hydrogen or a C1 to C10 alkyl group,

[Chemical Formula 5-2]

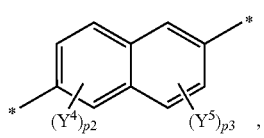

wherein, in Chemical Formula 5-2, $Y^4$ and $Y^5$ are the same or different, and are hydrogen, a C1 to C10 alkyl group, or a functional group represented by Chemical Formula 6, provided that at least one of $Y^4$ and $Y^5$ is the functional group represented by Chemical Formula 6, and p2 and p3 are the same or different and are integers ranging from 0 to 3, provided that p2 and p3 are not simultaneously zero,

[Chemical Formula 5-3]

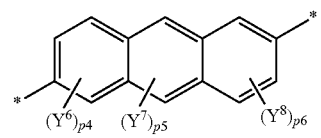

wherein, in Chemical Formula 5-3, $Y^6$ to $Y^8$ are the same or different, and are hydrogen, a C1 to C10 alkyl group, or a functional group represented by Chemical Formula 6, provided that at least one of $Y^6$ to $Y^8$ is the functional group represented by Chemical Formula 6, and p4 and p6 are the same or different and are integers ranging from 0 to 3, and p5 is an integer ranging from 0 to 2, provided that p4, p5, and p6 are not simultaneously zero,

[Chemical Formula 5-4]

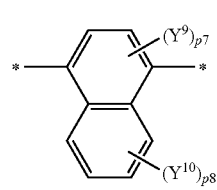

wherein, in Chemical Formula 5-4, $Y^9$ and $Y^{10}$ are the same or different, and are hydrogen, a C1 to C10 alkyl group, or a functional group represented by Chemical Formula 6, provided that at least one of $Y^9$ and $Y^{10}$ is the functional group represented by Chemical Formula 6, and p7 and p8 are the same or different and are integers ranging from 0 to 2, provided that p7 and p8 are not simultaneously zero,

[Chemical Formula 5-5]

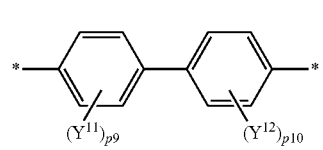

wherein, in Chemical Formula 5-5, $Y^{11}$ and $Y^{12}$ are the same or different, and are hydrogen, a C1 to C10 alkyl group, or a functional group represented by Chemical Formula 6, provided that at least one of $Y^{11}$ and $Y^{12}$ is the functional group represented by Chemical Formula 6, and p9 and p10 are the same or different and are integers ranging from 0 to 4, provided that p9 and p10 are not simultaneously zero,

[Chemical Formula 5-6]

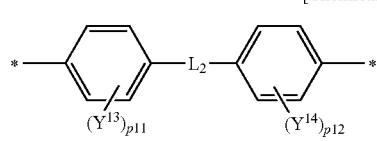

wherein, in Chemical Formula 5-6, $Y^{13}$ and $Y^{14}$ are the same or different, and are hydrogen, a C1 to C10 alkyl group, or a functional group represented by Chemical Formula 6, provided that at least one of $Y^{13}$ and $Y^{14}$ is the functional group represented by Chemical Formula 6, p11 and p12 are the same or different and are integers ranging from 0 to 4, $L_2$ is an ether group, a sulfide group, a ketone group, an amide group, a sulfoxide group, a sulfone group, an azo group, an imine group, a substituted or unsubstituted C1 to C20 alkylene group, a substituted or unsubstituted C2 to C20 alkenylene group, a substituted or unsubstituted C6 to C30 arylene group, a divalent hydrocarbon group which is unsubstituted or substituted with at least one functional group represented by Chemical Formula 6, or a divalent hydrocarbon group of Chemical Formulae 7-1 to 7-3, provided that both p11 and p12 are not zero when $L_2$ is unsubstituted with a functional group of Chemical Formula 6, and in Chemical Formula 5-1 to 5-6, at least one hydrogen of each aromatic ring is optionally substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$,

[Chemical Formula 6]

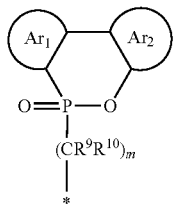

wherein, in Chemical Formula 6, $Ar_1$ and $Ar_2$ are the same or different and are a C4 to C30 substituted or unsubstituted aromatic cyclic group, $R^9$ and $R^{10}$ are the same or different, and are hydrogen, a C1 to C20 alkyl group, or a C6 to C30 aryl group, and m is an integer ranging from 0 to about 3,

[Chemical Formula 7-1]

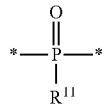

wherein, in Chemical Formula 7-1, $R^{11}$ is hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group,

[Chemical Formula 7-2]

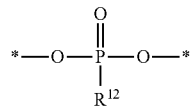

wherein, in Chemical Formula 7-2, $R^{12}$ is hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group,

[Chemical Formula 7-3]

2. The liquid crystalline thermoset oligomer or polymer of claim 1, wherein
the liquid crystalline thermoset oligomer has a number average molecular weight of about 500 to about 10,000 grams per mole, or the liquid crystalline thermoset polymer has a number average molecular weight of about 10,000 to about 1,000,000 grams per mole.

3. The liquid crystalline thermoset oligomer or polymer of claim 1, wherein
the structural unit of Chemical Formula 1 is included in an amount of about 5 mole percent to about 60 mole percent, based on the total amount of the liquid crystalline thermoset oligomer or polymer, and the structural unit of Chemical Formula 2 is included in an amount of about 40 mole percent to about 95 mole percent, based on the total amount of the liquid crystalline thermoset oligomer or polymer.

4. The liquid crystalline thermoset oligomer or polymer of claim 1, wherein
the liquid crystalline thermoset oligomer or polymer further comprises a structural unit of Chemical Formula 3:

[Chemical Formula 3]

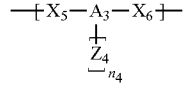

wherein, in Chemical Formula 3, $X_5$ to $X_6$ are the same or different, and are C(=O)O, O, C(=O)NR, NR', or CO, wherein R and R' are the same or different, and are hydrogen, a substituted or unsubstituted C1 to C20 alkyl group, or a substituted or unsubstituted C6 to C30 aryl group, $Z_4$ is a hydroxyl group, a thiol group, a substituted or unsubstituted maleimide group, a substituted or unsubstituted nadimide group, a substituted or unsubstituted tetrahydrophthalimide group, a substituted or unsubstituted C2 to C30 alkenyl group, a substituted or unsubstituted C2 to C30 alkynyl group, a substituted or unsubstituted propargyl ether group, a substituted or unsubstituted benzocyclobutene group, an (iso)cyanate group, a cyanide group, a substituted or unsubstituted C3 to C30 alicyclic group including a double bond or a triple bond, a substituted or unsubstituted heteroatom-containing C3 to C30 alicyclic group including a double bond or a triple bond, a C3 to C30 alicyclic group including a C2 to C30 alkenyl group or a C2 to C30 alkynyl group, a heteroatom-containing C3 to C30 alicyclic group including a C2 to C30 alkenyl group or a C2 to C30 alkynyl group, a C6 to C30 aryl group including a C2 to C30 alkenyl group or a C2 to C30 alkynyl group, a C6 to C30 aryl group including an (iso)cyanate group or a cyanide group, or a combination thereof, $n_4$ is an integer ranging from 0 to about 3, and $A_3$ is a functional group represented by Chemical Formulae 5-7 to 5-12,

[Chemical Formula 5-7]

wherein, in Chemical Formula 5-7, m1 and m2 are the same or different, and are integers ranging from 0 to about 3, and $R^5$ to $R^8$ are the same or different, and are hydrogen or a C1 to C10 alkyl group,

[Chemical Formula 5-8]

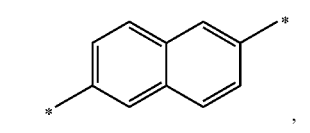

[Chemical Formula 5-9]

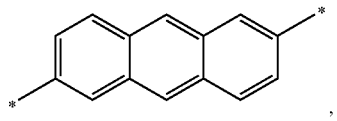

[Chemical Formula 5-10]

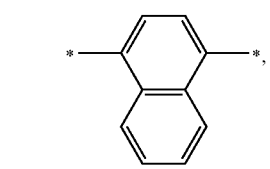

[Chemical Formula 5-11]

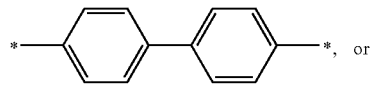, or

[Chemical Formula 5-12]

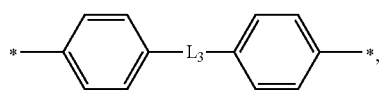, wherein, in Chemical Formula 5-12, $L_3$ is the same as $L_1$ of Chemical Formula 4-7, wherein, in Chemical Formulae 5-7 to 5-12, at least one hydrogen of each aromatic ring is optionally substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$.

5. The liquid crystalline thermoset oligomer or polymer of claim 4, wherein the structural unit of Chemical Formula 3 is included in an amount of about 0.01 to about 20 moles, based on 1 mole of the structural unit of Chemical Formula 2.

6. The liquid crystalline thermoset oligomer or polymer of claim 1, wherein $Z_1$ to $Z_3$ is a thermosetting cross-linking group represented by Chemical Formulae 8-1 to 8-7,

[Chemical Formula 8-1]

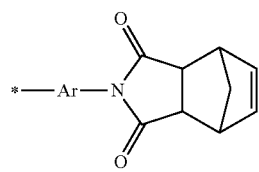

[Chemical Formula 8-2]

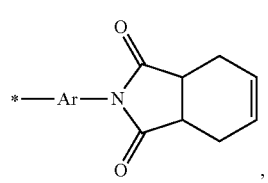

[Chemical Formula 8-3]

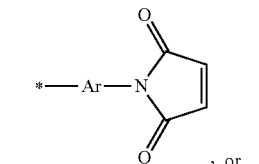, or

[Chemical Formula 8-4]

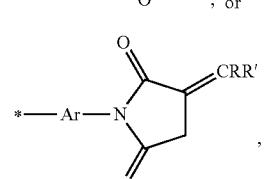, wherein, in Chemical Formula 8-4,

R and R' are the same or different, and are hydrogen, a substituted or unsubstituted C1 to C20 alkyl group, or a substituted or unsubstituted C6 to C30 aryl group,

[Chemical Formula 8-5]

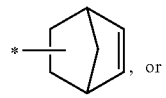, or

[Chemical Formula 8-6]

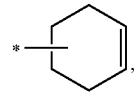, wherein, in Chemical Formulae 8-1 to 8-4,

Ar is a C6 to C30 arylene group, and in Chemical Formulae 8-1 to 8-6, at least one hydrogen of each alicyclic ring or aromatic ring is optionally substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group,

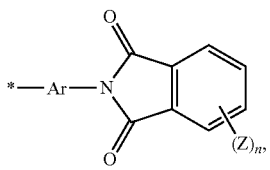

[Chemical Formula 8-7]

wherein, in Chemical Formula 8-7,
Ar is a C6 to C30 arylene group,
Z is a substituted or unsubstituted C2 to C20 alkenyl group, a substituted or unsubstituted C2 to C20 alkynyl group, or a substituted or unsubstituted C3 to C20 cycloalkenyl group, n is an integer ranging from 1 to about 4, and
in Chemical Formulae 8-7,
at least one hydrogen of each alicyclic ring or aromatic ring is optionally substituted with a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, or a substituted or unsubstituted C6 to C30 aryloxy group.

7. The liquid crystalline thermoset oligomer or polymer of claim 1, wherein $L_1$ of the above Chemical Formula 4-7 is an ether group, a sulfide group, a ketone group, an amide group, a sulfoxide group, a sulfone group, an azo group, an imine group, a substituted or unsubstituted C1 to C20 alkylene group, a substituted or unsubstituted C2 to C20 alkenylene group, a substituted or unsubstituted C6 to C30 arylene group, or a combination comprising at least one of the foregoing.

8. The liquid crystalline thermoset oligomer or polymer or claim 1, wherein
the functional group represented by Chemical Formula 6 comprises a functional group represented by Chemical Formula 11,

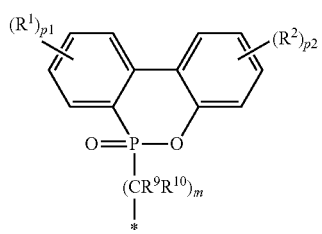

[Chemical Formula 11]

wherein, in Chemical Formula 11,
$R^1$ and $R^2$ are the same or different, and are hydrogen, a halogen, a substituted or unsubstituted C1 to C20 alkyl group, a substituted or unsubstituted C1 to C20 alkoxy group, a substituted or unsubstituted C3 to C20 cycloalkyl group, a substituted or unsubstituted C6 to C30 aryl group, a substituted or unsubstituted C7 to C30 arylalkyl group, a substituted or unsubstituted C6 to C30 aryloxy group, or $Z_1$,
p1 and p2 are the same or different and are integers ranging from 0 to 4, and
$R^9$ and $R^{10}$ are the same or different, and are hydrogen, a C1 to C20 alkyl group, or a C6 to C30 aryl group, and
m is an integer ranging from 0 to about 3.

9. A thermosetting composition comprising the liquid crystalline thermoset oligomer or polymer of claim 1.

10. The thermosetting composition of claim 9, wherein the thermosetting composition further comprises a polar aprotic solvent.

11. The thermosetting composition of claim 10, wherein the polar aprotic solvent comprises N-methylpyrrolidone, dimethyl sulfoxide, N,N'-dimethyl formamide, N,N'-diethylformamide, N,N'-dimethyl acetamide, N,N'-dimethyl acetamide, N-methylpropionamide, N-methylcaprolactam, γ-butyrolactone, dimethylimidazolidinone, tetramethylphosphoric amide, ethylcellosolve acetate, methylethylketone, propylene glycol monomethyl ether acetate, or a combination thereof.

12. The thermosetting composition of claim 9, wherein the thermosetting composition comprises about 0.1 to about 300 parts by weight of the liquid crystalline thermosetting oligomer or polymer of claim 1, based on 100 parts by weight of a solvent.

13. The thermosetting composition of claim 9, wherein the thermosetting composition further comprises a maleimide cross-linking agent.

14. The thermosetting composition of claim 9, wherein the thermosetting composition further comprises an epoxy compound.

15. A prepreg comprising a polymerization product of the thermosetting composition according to claim 9.

16. A film comprising a polymerization product of the thermosetting composition according to claim 9.

17. A board comprising a polymerization product of the thermosetting composition according to claim 9.

18. The board of claim 17, wherein the board further comprises a prepreg comprising the polymerization product of the thermosetting composition according to claim 9.

19. The board of claim 18, wherein the board is disposed on a surface of the prepreg.

20. The board of claim 19, wherein a surface of a flexible printed circuit comprising the prepreg further includes a conductor pattern.

* * * * *